US010350349B2

(12) United States Patent
Gravesen et al.

(10) Patent No.: US 10,350,349 B2
(45) Date of Patent: Jul. 16, 2019

(54) MEDICINE DELIVERY DEVICE WITH RESTRICTED ACCESS FILLING PORT

(71) Applicant: CeQur SA, Horw (CH)

(72) Inventors: Peter Gravesen, Nordborg (DK); Claus E. Jensen, Hillerød (DK); Heiko Arndt, Flensbrgo (DE); Patrick McDermott, Oxford, MA (US); Mads Dall, Hellerup (DK)

(73) Assignee: Cequr SA, Horw (CH)

( * ) Notice: Subject to any disclaimer, the term of this patent is extended or adjusted under 35 U.S.C. 154(b) by 421 days.

(21) Appl. No.: 14/717,697

(22) Filed: May 20, 2015

(65) Prior Publication Data

US 2016/0008536 A1    Jan. 14, 2016

Related U.S. Application Data

(60) Provisional application No. 62/000,771, filed on May 20, 2014.

(51) Int. Cl.
| A61M 5/142 | (2006.01) |
| F16L 29/02 | (2006.01) |
| A61M 39/00 | (2006.01) |

(52) U.S. Cl.
CPC ......... *A61M 5/14248* (2013.01); *F16L 29/02* (2013.01); *A61M 2005/1426* (2013.01); *A61M 2039/009* (2013.01); *A61M 2209/045* (2013.01)

(58) Field of Classification Search
CPC .... A61M 5/14248; A61M 2005/14268; A61M 2209/086; A61M 5/1413; A61M 2209/045; A61M 2039/009
See application file for complete search history.

(56) References Cited

U.S. PATENT DOCUMENTS

| 4,364,387 A | 12/1982 | Larkin |
| 4,557,722 A | 12/1985 | Harris |
| 4,568,335 A | 2/1986 | Updike et al. |
| 4,883,472 A | 11/1989 | Michel |
| 5,049,129 A | 9/1991 | Zdeb et al. |
| 5,057,076 A | 10/1991 | Polaschegg |
| 5,078,683 A | 1/1992 | Sancoff et al. |
| 5,216,597 A | 6/1993 | Beckers |

(Continued)

FOREIGN PATENT DOCUMENTS

| CA | 1159736 A | 1/1984 |
| CA | 2534726 A1 | 3/2005 |

(Continued)

OTHER PUBLICATIONS

International Search Report and Written Opinion dated Oct. 26, 2015, for PCT Application PCT/IB2015/001592, 9 pages.

(Continued)

*Primary Examiner* — Emily L Schmidt
(74) *Attorney, Agent, or Firm* — Eversheds Sutherland (US) LLP

(57) ABSTRACT

A disposable patch pump may be provided with a filling adapter, to ensure filling by an authorized user. The adapter mates with the pump and a source of medicament, such as an insulin vial, to prevent filling the pump directly with a conventional syringe. The adapter and/or pump filling port may be configured with a frangible element, to limit the system to single use.

23 Claims, 22 Drawing Sheets

(56) References Cited

U.S. PATENT DOCUMENTS

| | | | |
|---|---|---|---|
| 5,317,506 | A | 5/1994 | Coutre et al. |
| 5,334,162 | A | 8/1994 | Harris |
| 5,383,865 | A | 1/1995 | Michel |
| 5,527,288 | A | 6/1996 | Gross et al. |
| 5,545,152 | A | 8/1996 | Funderburk et al. |
| 5,547,470 | A | 8/1996 | Johnson et al. |
| 5,879,143 | A | 3/1999 | Cote et al. |
| 6,126,637 | A | 10/2000 | Kriesel et al. |
| 6,186,982 | B1 | 2/2001 | Gross et al. |
| 6,235,004 | B1 | 5/2001 | Steenfeldt-Jensen et al. |
| 6,277,095 | B1 * | 8/2001 | Kriesel ............... A61M 5/152 128/DIG. 12 |
| 6,482,185 | B1 | 11/2002 | Hartmann |
| 6,482,186 | B1 | 11/2002 | Douglas et al. |
| 6,585,016 | B1 * | 7/2003 | Falligant ............ A61M 16/183 128/202.22 |
| 6,656,159 | B2 | 12/2003 | Flaherty |
| 6,872,200 | B2 | 3/2005 | Mann et al. |
| 7,648,494 | B2 | 1/2010 | Kornerup et al. |
| 7,758,548 | B2 | 7/2010 | Gillespie et al. |
| 7,910,151 | B2 | 3/2011 | Uhland et al. |
| 7,918,832 | B2 | 4/2011 | Veasey et al. |
| 7,938,801 | B2 | 5/2011 | Hawkins et al. |
| 7,988,675 | B2 | 8/2011 | Gillespie, III et al. |
| 8,202,250 | B2 | 6/2012 | Stutz, Jr. |
| 8,273,061 | B2 | 9/2012 | McConnell et al. |
| 8,285,328 | B2 | 10/2012 | Caffey et al. |
| 8,353,878 | B2 | 1/2013 | Moller et al. |
| 8,372,039 | B2 | 2/2013 | Mernoe et al. |
| 8,382,696 | B2 | 2/2013 | Beiriger et al. |
| 8,395,591 | B2 | 3/2013 | Kruglick |
| 8,409,143 | B2 | 4/2013 | Lanigan et al. |
| 8,434,528 | B2 | 5/2013 | Ibranyan et al. |
| 8,444,597 | B2 | 5/2013 | Sullivan et al. |
| 8,460,244 | B2 | 6/2013 | Srisathapat et al. |
| 8,500,716 | B2 | 8/2013 | Adair et al. |
| 8,540,673 | B2 | 9/2013 | Hines et al. |
| 8,547,239 | B2 | 10/2013 | Peatfield et al. |
| 8,551,045 | B2 | 10/2013 | Sie et al. |
| 8,556,865 | B2 | 10/2013 | Krulevitch et al. |
| 8,574,201 | B2 | 11/2013 | Chattaraj et al. |
| 8,579,853 | B2 | 11/2013 | Reggiardo et al. |
| 8,585,657 | B2 | 11/2013 | Colton |
| 8,603,034 | B2 | 12/2013 | Lynch et al. |
| 8,613,724 | B2 | 12/2013 | Lanier, Jr. et al. |
| 8,647,296 | B2 | 2/2014 | Moberg et al. |
| 8,679,062 | B2 | 3/2014 | Yodfat et al. |
| 2003/0229310 | A1 | 12/2003 | Flaherty et al. |
| 2007/0255235 | A1 | 11/2007 | Olsen et al. |
| 2010/0094215 | A1 | 4/2010 | Grant et al. |
| 2010/0198182 | A1 | 8/2010 | Lanigan et al. |
| 2010/0217105 | A1 | 8/2010 | Yodfat et al. |
| 2010/0264028 | A1 | 10/2010 | Pang |
| 2010/0274196 | A1 | 10/2010 | Brandt et al. |
| 2011/0054285 | A1 | 3/2011 | Searle et al. |
| 2011/0060280 | A1 | 3/2011 | Caffey et al. |
| 2011/0160696 | A1 | 6/2011 | Hoss |
| 2012/0022450 | A2 | 1/2012 | De Polo |
| 2012/0261027 | A1 | 10/2012 | Py |
| 2013/0116632 | A1 | 5/2013 | Yavorsky et al. |
| 2013/0245545 | A1 | 9/2013 | Arnold et al. |
| 2013/0253430 | A1 | 9/2013 | Kouyoumjian et al. |
| 2013/0310800 | A1 | 11/2013 | Yodfat et al. |
| 2013/0310801 | A1 | 11/2013 | Yodfat et al. |

FOREIGN PATENT DOCUMENTS

| | | |
|---|---|---|
| EP | 0032792 A2 | 7/1981 |
| EP | 1 346 737 A1 | 9/2003 |
| EP | 2125077 A2 | 12/2009 |
| EP | 2134390 A1 | 12/2009 |
| EP | 2531232 A2 | 12/2012 |
| EP | 2548595 A1 | 1/2013 |
| EP | 2611478 A1 | 7/2013 |
| EP | 2630980 A1 | 8/2013 |
| IL | 61891 A | 12/1983 |
| WO | WO-1996013293 A1 | 5/1996 |
| WO | WO-2005016558 A2 | 2/2005 |
| WO | WO-2008008845 A2 | 1/2008 |
| WO | WO-2008020447 A1 | 2/2008 |
| WO | WO-2008078318 A2 | 7/2008 |
| WO | WO-2008139460 A2 | 11/2008 |
| WO | WO-2009016636 A2 | 2/2009 |
| WO | WO-2009016637 A2 | 2/2009 |
| WO | WO-2010089607 A1 | 8/2010 |
| WO | WO-20110133823 A1 | 10/2011 |
| WO | WO-2012032411 A2 | 3/2012 |
| WO | WO-20120145752 A2 | 10/2012 |
| WO | WO-2013188703 A1 | 12/2013 |
| WO | WO-2014029416 A1 | 2/2014 |

OTHER PUBLICATIONS

Maude, "Roche insulin delivery systems inc. accu-chek spirit insulin infusion pump" <http://www.accessdata.fda.gov/scripts/cdrh/cfdocs/cfMAUDE/Detail.CFM?MDRFOI_ID=1811123>, downloaded on Nov. 11, 2015, 3 pages.

* cited by examiner

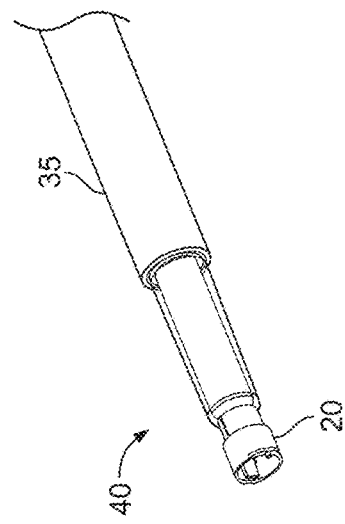
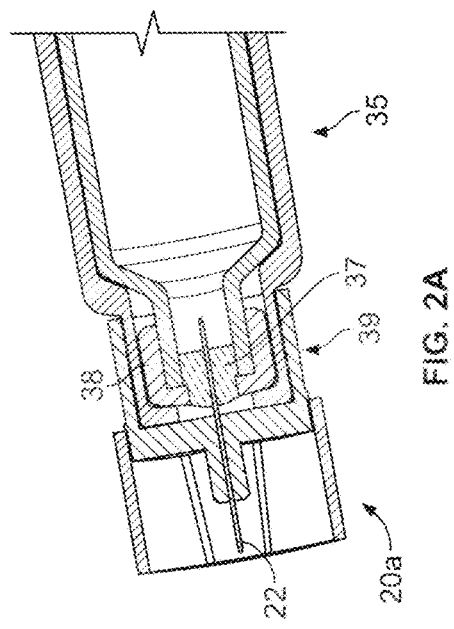
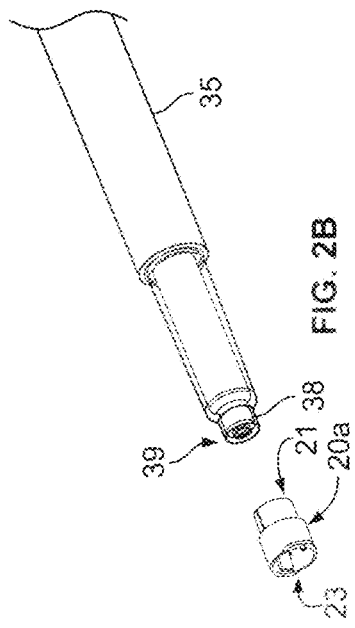
FIG. 2A
FIG. 2B
FIG. 2C

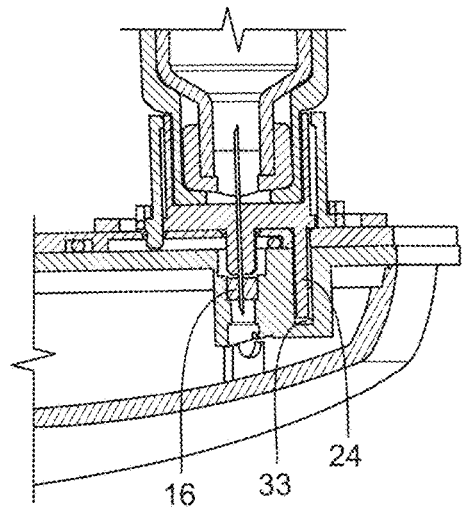
FIG. 3E
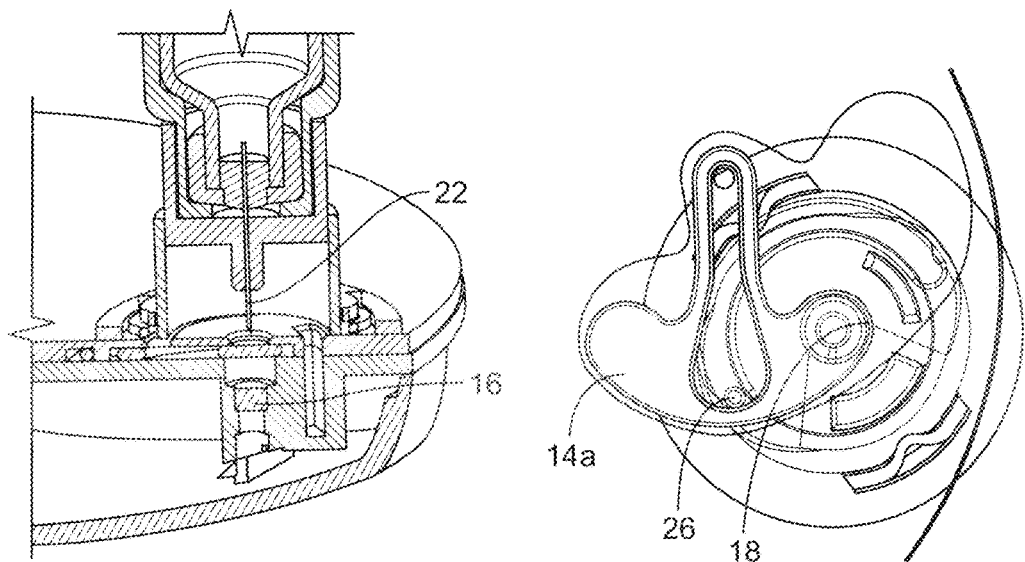
FIG. 3F
FIG. 3G

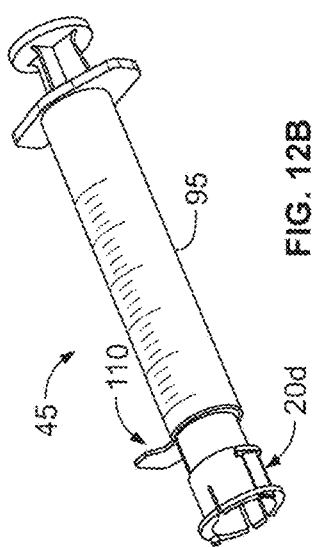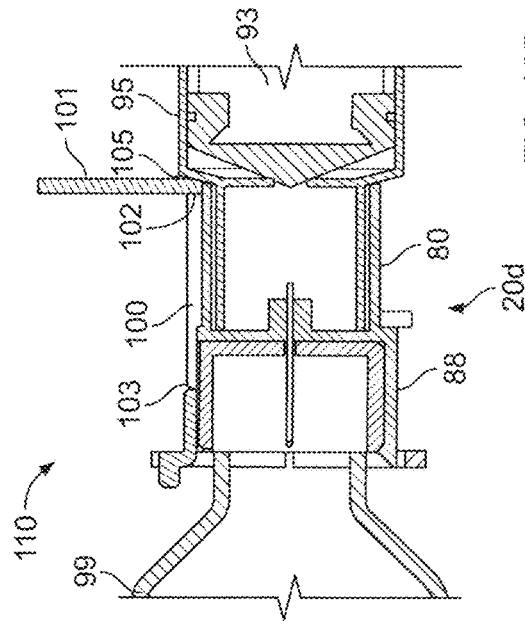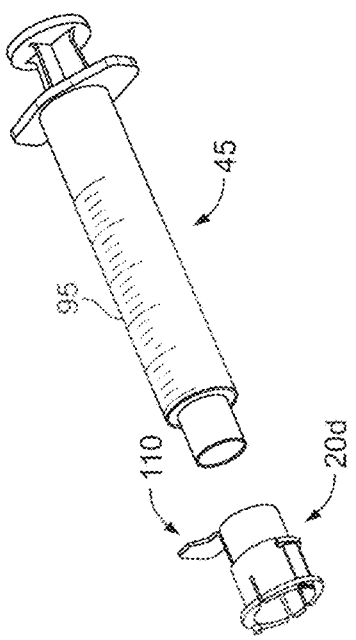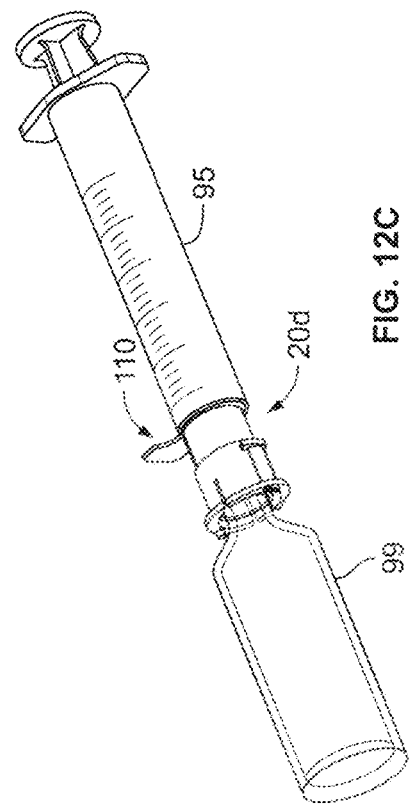
FIG. 12A
FIG. 12B
FIG. 12C
FIG. 12D

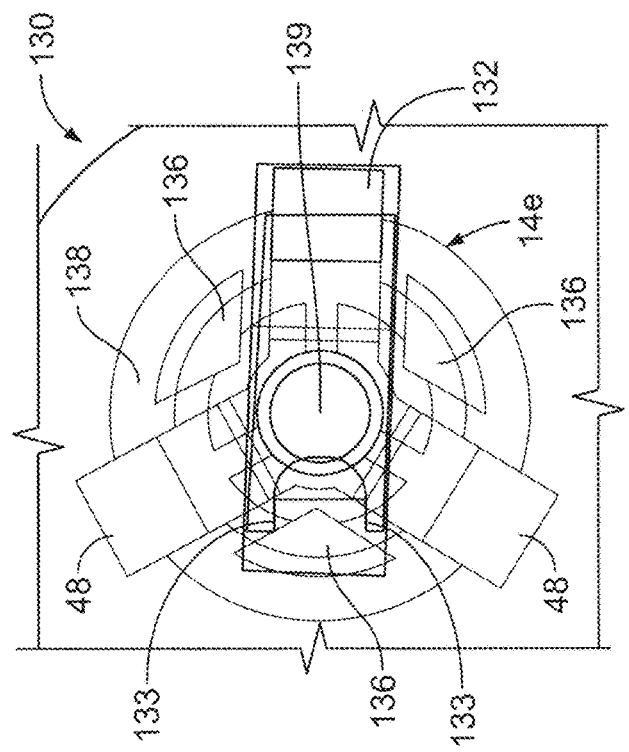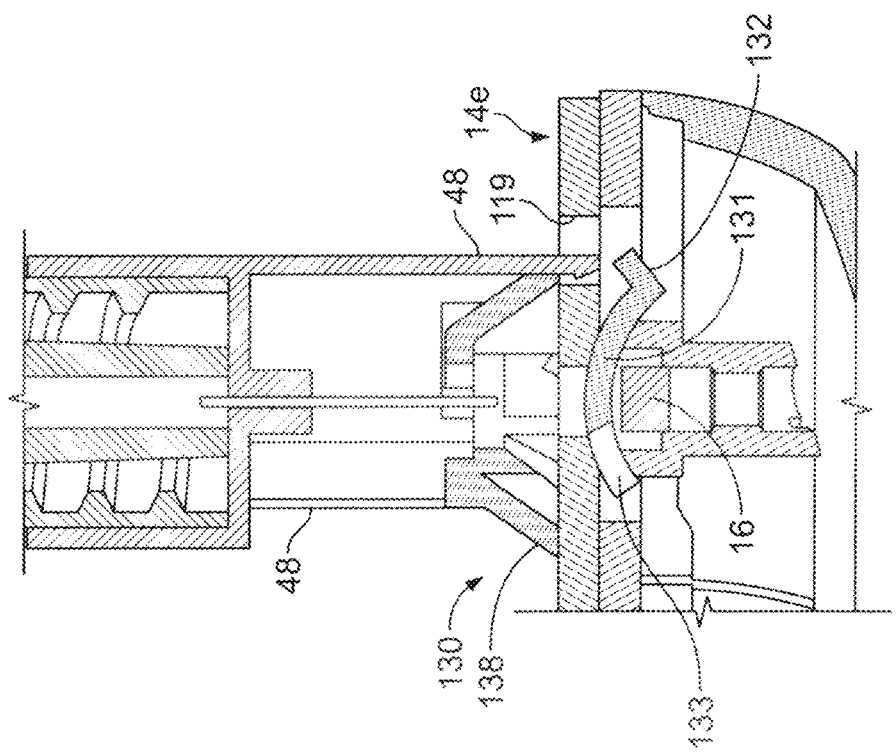

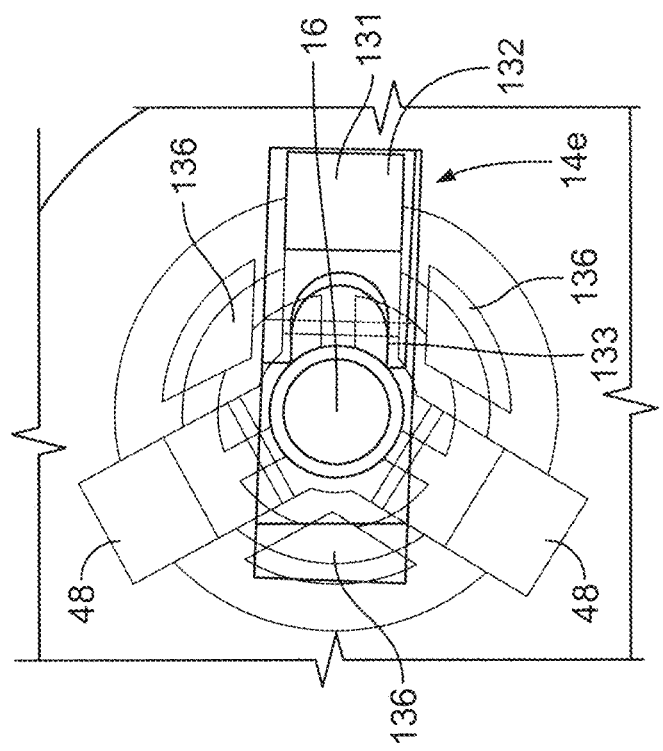
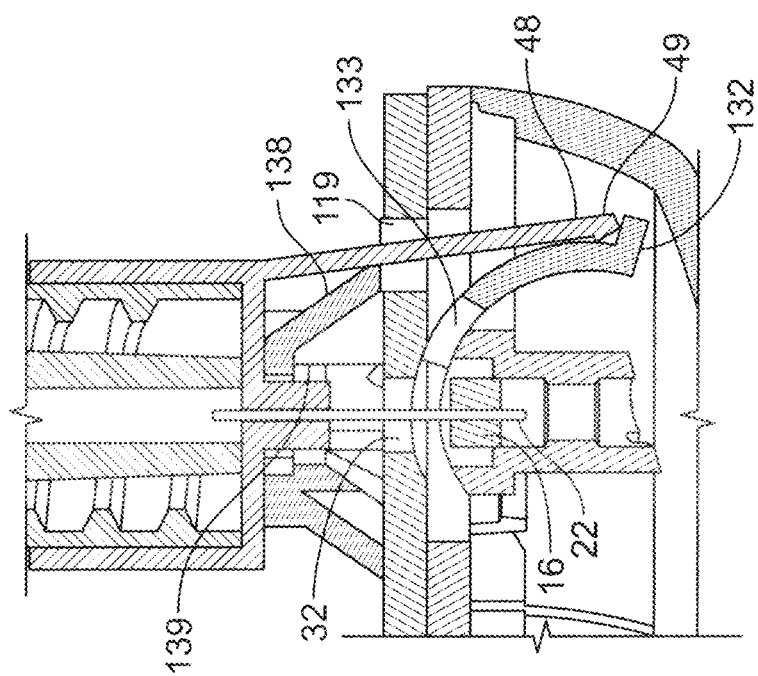
FIG. 16F
FIG. 16E

MEDICINE DELIVERY DEVICE WITH RESTRICTED ACCESS FILLING PORT

CROSS-REFERENCE TO RELATED APPLICATION

This application claims priority to and the benefit of U.S. Provisional Patent Application No. 62/000,771 filed on May 20, 2014, which is incorporated herein in its entirety by reference.

TECHNICAL FIELD OF THE INVENTION

The invention relates generally to wearable infusion pump devices (e.g., patch pumps) and other medical delivery devices having a filling port for filling the device with medicament and, more particularly, to systems and methods for preventing unauthorized filling of the device.

BACKGROUND

Infusion devices (e.g., the infusion device described in U.S. Pat. No. 8,547,239, the contents of which are incorporated by reference as if set forth herein in their entirety) are often used to deliver medicament (e.g., insulin) to a user. With many insulin infusion devices, there is no physical restriction on the types of substances that can be used to fill the devices. Typically, an exposed septum on the device can be pierced by a hollow needle, allowing for the transfer of any substance that can move through the hollow needle into the device. This can lead to unintended uses and pose a risk to the user.

SUMMARY OF THE INVENTION

It is therefore desirable to provide systems and methods to restrict access to a filling port of an infusion device, for safety and other reasons. An objective of the invention is to provide a lock and key type filling interface, in which the pump body includes one or more components forming a portion of the lock and an adapter forms corresponding mating key components. In this manner, access to fill the pump is limited to individuals possessing the adapter key, the manufacture and distribution of which may be suitably controlled. In one embodiment, a shutter and/or a valve may only be opened with the key, which key may have a specific mechanical shape, a specific distance between a needle and a coupling feature, and/or a specific length of the coupling feature. One or more components of the lock and key may be made sterile, as necessary, and single use features may be incorporated in the pump and/or adapter components to preclude unauthorized reuse of single-use components.

Another objective of the invention to prevent user error. One type of user error occurs when an incorrect type of medicament is used. By limiting delivery of the adapter with a specific type(s) of insulin, it is unlikely the adapter would be used with another, unauthorized medicament container. Another form of user error can occur through needle injury, such as "sticking" Certain features (e.g., the key) can be designed to protect against needle injury, such as by recessing the needle relative to another surface or covering the needle. User error may also occur when a user injects medicament into any other soft element (e.g., soft control buttons) on the patch pump device and not the filling port septum. Protecting the septum may make it difficult, if not impossible, to fill the device through any access other than the filling port, which filling port may only be accessed with the key. This configuration is especially useful in patch pumps and other medical delivery devices with a single port, although this configuration can also be used with multiple port pumps.

Embodiments of insulin and other medicament infusion devices, such as disposable patch pumps that adhere to a patient's skin, include a restricted insulin filling port. In one embodiment, the filling port includes a movable cover mechanism (e.g., a shutter) that obstructs access to the filling port or a portion of the port, such as a needle piercing septum. The shutter can be automatically retracted to expose the septum when a unique adapter is mated with the filling port.

Some embodiments have a sliding, rotating, or cantilevered shutter that is retracted, moved, or displaced with an adapter to provide access to the septum for filling the device with insulin. The adapter may uniquely interface with a housing of the device, so that the shutter may only be opened with a specific matching adapter, e.g., through a unique mating configuration or design. In some embodiments, the adapter is inserted into the patch pump base and rotated to shift or retract the shutter. A medicament container (e.g., a syringe, a pen, a cartridge, or a vial containing insulin or other medicament) may be coupled to the adapter and used to fill the patch pump. Embodiments of the system advantageously prevent filling of the patch pump directly with a conventional syringe.

In one embodiment, the adapter is disposed at the end of an insulin delivery apparatus (or a medicament container) and provided with a standard 3 mL cartridge of insulin. To couple the medicament container to the device, the adapter is pushed into the pump base and rotated to open the shutter and expose the septum. The delivery apparatus is pushed further and then the cartridge is emptied into the pump reservoir. In another embodiment, the vehicle is preloaded with insulin instead of using a removable cartridge. In still another embodiment, the adapter may be used to secure a vial for withdrawing fluid into the delivery apparatus syringe, and the same adapter may be used to couple the device to the pump and fill the pump with insulin. In yet another embodiment, a vial may be coupled directly to the adapter which couples directly to the device. Various combinations of elements and kits can be delivered together, including pump(s), adapters, syringes, and medicament containers (e.g., vials, cartridges, pens, etc.).

In one aspect, the invention relates to a patch pump system. The patch pump system has a patch pump device with a filling port and a shutter proximate the filling port movable between a closed position and an open position and adapted to prevent access to the filling port in the closed position. The patch pump system also has a filling adapter adapted to be coupled to the filling port and move the shutter from the closed position to the open position.

In one embodiment of the above aspect, the filling port has a septum. The filling port may be accessible from a user contact side of the patch pump device. In some embodiments, the shutter is accessible from a user contact side of the patch pump device. The shutter may be disposed within the patch pump device, and the shutter may be disposed within the filling port. The shutter can define a shutter opening, such that the shutter is in the open position when the shutter opening is aligned with a septum of the filling port. In some embodiments, the shutter is a valve or further includes a valve.

In some embodiments of the above aspect, the patch pump device defines a device opening for coupling the filling adapter to the filling port and enabling controlled movement of the shutter. The filling adapter may have a mating surface adapted to fit in the device opening. The mating surface may have a protrusion and/or the mating surface may be adapted to contact the shutter. In certain embodiments, the filling adapter has a hollow needle. The needle may be exposed on two sides and be adapted to pierce two septa simultaneously. A first end of the filling adapter may be adapted to mate with a medicament container, which may be medicament container may be a syringe, a pen, a cartridge, and/or a vial. In some embodiments the patch pump system also has a socket adapted to receive the filling adapter, which socket may be adapted to support rotation of the filling adapter.

In another aspect, the invention relates to a filling adapter for use with a patch pump device. The filling adapter has a first end adapted to mate with a medicament container and a second end adapted to couple to a filling port of a patch pump device and to move a shutter of the patch pump device from a closed position to an open position.

In some embodiments of the above aspect, the first end defines a recess for receiving the medicament container. The first end may have a needle for piercing the medicament container. The medicament container may be a syringe, a pen, a cartridge, and/or a vial. The second end may have a needle. In certain embodiments, the second end has a protrusion adapted to extend into the patch pump device, such as a resilient tab. At least one of the first end and the second end may have a frangible component adapted to break after a single use.

In another aspect, the invention relates to a method of filling a patch pump device. The method includes coupling a first end of a filling adapter to a medicament container, coupling a second end of the filling adapter to a filling port on a patch pump device to move a shutter proximate the filling port from a closed position preventing access to the filing port to an open position allowing access to the filling port, and filling a reservoir of the patch pump device with medicament from the medicament container via the filling port.

In some embodiments of the above aspect, coupling the first end of the filling adapter to the medicament container includes receiving at least a portion of the medicament container in a recess of the filling adapter. Coupling the first end of the filling adapter to the medicament container may include piercing the medicament container with a needle. Coupling the second end of the filling adapter to the filling port on the patch pump device may include inserting a mating surface of the second end into the patch pump device, and may include rotating the filling adapter to move the shutter. In certain embodiments, the inserting step moves the shutter to the open position. The medicament container may be a syringe, a pen, a cartridge, and/or a vial. Filling the reservoir can include transferring medicament from the medicament container under pressure. The method may also include, after coupling the first end of the filling adapter to the medicament container, drawing medicament into the medicament container. The medicament may be drawn from a vial coupled to the second end.

In another aspect, the invention relates to a patch pump device. The patch pump device has a filling port and a shutter proximate the filling port movable between a closed position and an open position and adapted to prevent access to the filling port when in the closed position, wherein the shutter comprises at least one mating surface adapted to couple to a filling adapter to move the shutter to the open position.

In another aspect, the invention relates to a filling system adapted for use with a patch pump device. The filling system includes a filling adapter having a first end adapted to receive a medicament container and a second end adapted to mate with a filling port of a patch pump device and move a shutter of the patch pump device from a closed position to an open position. The filling system also includes a medicament container.

In another aspect, the invention relates to a patch pump kit. The patch pump kit includes a patch pump device with a filling port and a shutter proximate the filling port movable between a closed position and an open position and adapted to prevent access to the filling port when in the closed position. The patch pump kit also includes a filling adapter with a first end adapted to receive a medicament container and a second end adapted to mate with the filling port and move from the closed position to the open position. The patch pump kit also includes a medicament container.

In another aspect, the invention relates to a filling adapter kit. The filling adapter kit includes a medicament container adapter, a syringe adapter, and a pump device filling port adapter.

In some embodiments of the above aspect, at least a portion of the syringe adapter is adapted to actuate a shutter disposed in a pump device to move the shutter from a closed position to an open position.

In another aspect, the invention relates to a patch pump kit. The patch pump kit includes a patch pump device with a filling port and a shutter movable between a closed position and an open position and adapted to prevent access to the filling port in the closed position. The patch pump kit also includes a filling pump device adapted to mate with the filling port and move the shutter to the open position. The filling pump device includes an inlet for receiving a medicament container, an outlet for mating with the filling port, and a pump for transferring medicament from the inlet to the outlet. The patch pump kit also includes an adapter for mating the medicament container to the inlet.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2A shows a cross-sectional view of the adapter key of FIG. 1A coupled to a medicament container in accordance with some embodiments of the present invention;

FIGS. 2B and 2C show perspective views of a medicament delivery system with the adapter key of FIG. 1A in accordance with some embodiments of the present invention;

FIG. 3E shows cross-sectional detail of the coupled medicament delivery system of FIG. 3A in which the shutter is in the open position in accordance with some embodiments of the present invention and the needle has pierced a septum fluidically coupled to a reservoir in the patch pump system in accordance with some embodiments of the present invention;

FIG. 3F shows a cross-sectional detail of the coupled medicament delivery system of FIG. 3A in which the needle has been retracted and the shutter has been re-closed to a second position in accordance with some embodiments of the present invention;

FIG. 3G shows a bottom view of the medicament delivery system and patch pump system of FIG. 3A with the shutter re-closed to the second position in accordance with some embodiments of the present invention;

FIGS. 12A and 12B show perspective views of an illustrative embodiment of a syringe-type medicament delivery system having the adapter key of FIG. 11A in accordance with the present invention;

FIG. 12C shows a perspective view of the safety-tabbed syringe-type medicament delivery system of FIGS. 11A and 11B and a medicament vial in accordance with the present invention;

FIG. 12D shows a cross-sectional view of the safety-tabbed adapter key of FIG. 11A coupled to a medicament vial in accordance with some embodiments of the present invention;

FIG. 16A shows a cross-sectional detail of the coupled medicament delivery system of FIG. 15B with the arcuate shutter in a closed position in accordance with some embodiments of the present invention;

FIG. 16B shows a bottom view of the coupled shutter and adapter key of FIG. 16A in accordance with some embodiments of the present invention;

FIG. 16E shows cross-sectional detail of the coupled medicament delivery system of FIG. 15B with the hollow needle piercing the septum of the patch pump system in accordance with some embodiments of the present invention;

FIG. 16F shows a bottom view of the coupled shutter and adapter key of FIG. 16E in accordance with some embodiments of the present invention;

DETAILED DESCRIPTION

Figure 1A:
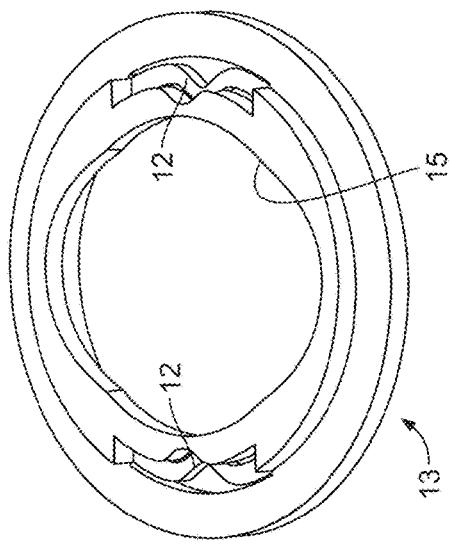
FIG. 1A shows a perspective view of an illustrative embodiment of an adapter key in accordance with the present invention.
Figure 1C:
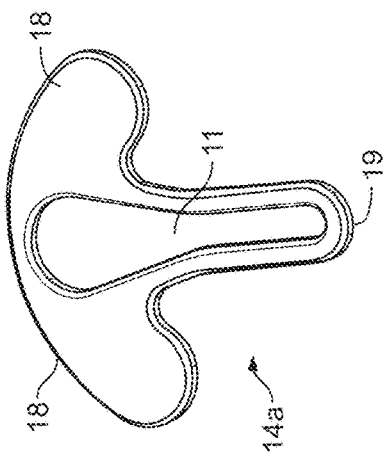
FIG. 1C shows a perspective view of an illustrative embodiment of a socket in accordance with the present invention.

A patch pump system 30 and uniquely-keyed medicament delivery system 40 in accordance with one embodiment of the present invention are depicted in FIGS. 1A-3G. Advantageously, the patch pump system 30 and keyed medicament delivery system 40 are structured and arranged to mate or couple with a guiding socket 13 to provide a lock-and-key-type filling interface. In this manner, access for filling a medicament reservoir or pump 17 of the patch pump system 30 is limited to individuals possessing the filling adapter or adapter key 20a, the manufacture and distribution of which may be suitably controlled to prevent coupling with and/or filling the patch pump system 30 using unauthorized or improper medicaments, or by unauthorized individuals.

In some implementations of the embodiment, the patch pump system 30 includes a guiding socket 13, a key-lock filling port 32, and a movable, e.g., rotatable, shutter 14a that are integrated on or into the user contact side 31 of the patch pump system 30. The socket 13, which may be disposed on the surface of the user contact side 31, is provided as an initial guide for the adapter key 20a. For example, the socket 13 may define an opening 15 and may be shaped and dimensioned to accommodate the outer peripheral surface and/or a rim 25 of the adapter key 20a. In some variations, the socket 13 may also include one or more elastic expansion elements 12 that are structured and arranged to displace radially when the adapter key 20a is inserted into and rotated within the socket opening 15 and oriented to position the shutter 14a in an open (uncovered) state.

Figure 1B:
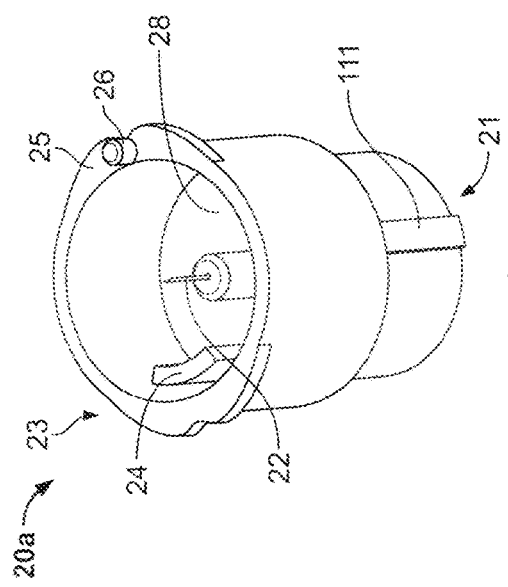
FIG. 1B shows a cross-sectional view of the adapter key of FIG. 1A in accordance with some embodiments of the present invention.
Figure 1D:
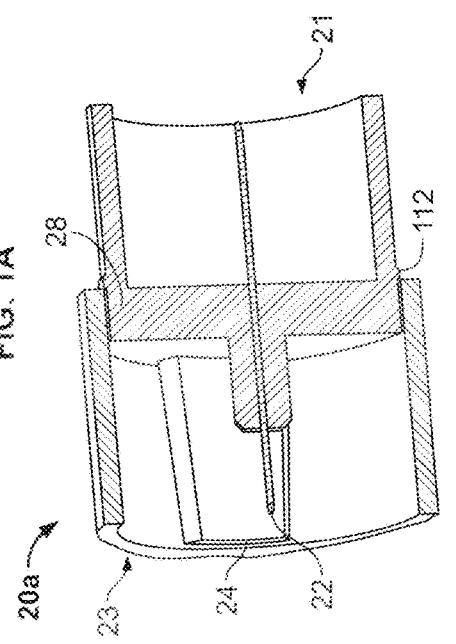
FIG. 1D shows a top view of an illustrative embodiment of a shutter in accordance with the present invention.

The shutter 14a may be configured to cover and uncover a septum 16 that seals the reservoir or pump 17. As shown in FIG. 1D, the shutter 14a may have a rounded T-shape having a central portion 19 and two wing portions 18. A central, elongate opening 11 adapted to receive a protrusion 26 of the adapter key 20a and a pin 29 about which the shutter 14a may rotate, may be provided in the central portion 19 of the shutter 14a. In some implementations, the shutter 14a is disposed beneath the user contact side 31 of the patch pump system 30 (FIG. 3B), such that the pin 29 is disposed within a distal end of the elongate opening 11. In operation, the shutter 14a is configured to rotate about the pin 29 upon application of a rotating force or torque to the protrusion 26 of the adapter key 20a. Although the shutter 14a has been described as having a rounded T-shape, those of ordinary skill in the art can appreciate that a myriad of, for example, rounded and polygonal shapes may be used to effect the purpose and function of the shutter 14a. For example, the shutter may be L-shaped, I-shaped, rectangular, triangular, and so forth.

The key-lock filling port 32 includes an opening in the user contact side 31 of the patch pump system 30 and the septum 16, which may be pierced, e.g., by a hollow needle 22, before the reservoir or pump 17 can be filled with a measured amount of medicament. The shutter 14a covers and uncovers the filling port 32, respectively, to protect the septum 16 from and to expose the septum 16 to the needle 22 of the adapter key 20a. In addition to the shutter 14a, the patch pump system 30 may also include a receptacle 33 to provide another degree of security from improper medicament containers 35. For example, the receptacle 33 may be adapted to position the medicament delivery system 35 in a desired location before enabling delivery of a measured amount of medicament and, moreover, may be dimensioned to receive a safety protrusion 24 that may be formed in the adapter key 20a. Advantageously, the safety protrusion 24 and receptacle 33 are structured and arranged to mate or couple, so that, only when a proper medicament container 35 is being used can the safety protrusion 24 advance into the receptacle 33, enabling the hollow needle 22 to penetrate the septum 16.

As shown in FIGS. 2A-2C, the keyed medicament delivery system 40 includes a medicament container 35, e.g., a pen and/or a cartridge pre-filled with a measured amount of insulin, and an adapter key 20a that provides a fluidic connection between the medicament container 35 and a reservoir 17 in the patch pump device 30, e.g., for the purpose of filling the reservoir 17 with a measured amount of a medicament. As shown in FIGS. 1A and 1B, in some implementations, the adapter key 20a includes a first end 21 and a second end 23, each of which includes a hollow, cylindrical or substantially cylindrical portion. The hollow portions of the first end 21 and second end 23 are separated by a wall 28 through which a hollow needle 22 passes. To protect a user against inadvertently sticking the user or another, the hollow needle 22 may be contained or recessed within the adapter key 20a or, more particularly, within the hollow portions at the first 21 and second ends 23 of the adapter key 20a.

The first end 21 and the second end 23 of the adapter key 20a may be movable with respect to each other, such that the medicament container 35 can be urged to force the hollow needle 22 through the septum 16 of the filling port 32, e.g., by sliding, e.g., in an axial direction, the first end 21 of the adapter key 20a relative to the second end 23 of the adapter key 20a. The first end 21 may include a raised, alignment device 111 formed on the outer, peripheral surface of the first end 21. The alignment device 111 can be structured and arranged to mate or couple with a receiving groove or track defined by the inner surface of the second end 23. The groove or track may be dimensioned to receive the alignment device 111. The alignment device 111 and groove combination position and guide the first end 21 with respect to the second end 23 while the first end 21 slidingly translates into and within the second end 23 during the septum piercing process and medicament delivery. The first end 21 of the adapter key 20a is further configured to receive and to pierce a septum or seal 37 of the medicament container, e.g., by axial pressing and/or twisting, while the second end 23 of the adapter key 20a may be coupled to the socket 13 of the patch pump device 30.

As shown in FIGS. 2A-2C, the first end 21 is adapted to mate with a medicament container 35 at a first end 39 thereof. In some variations, the first end 39 of the medicament container 35 includes a fitting 38 for releasably connecting, e.g., by close sliding fit, with threadings, or the like, the medicament container 35 to the first end of 21 the adapter key 20a. When the adapter key 20a is properly attached to the medicament container 35, the hollow needle 22 of the adapter key 20a is located to pierce the septum 37 of the medicament container 35, during attachment. Referring also to FIG. 1B, the first end 21 of the adapter key 20a may also include an additional safety feature, e.g., a safety protrusion 24, that is cantilevered axially from the wall 28. The safety protrusion 24 is configured to prevent the premature deployment of the needle 22, e.g., until the filling port shutter 14a is opened and the needle 22 and the septum 16 are properly aligned. Once mated in a receptacle 33 in the patch pump system 30, the safety protrusion 24 aligns with the receptacle 33 (FIG. 3C) to enable advancement of the needle 22 into and through the septum 16.

Referring to FIG. 1A, in some variations, the second end 23 of the adapter key 20a may include a rim 25 having a desired shaped and dimensions and on which a protrusion 26 is formed. Advantageously, the shape and dimension of the rim 25 can be selected to mate with the opening 15 of the socket 13 on the user contact side 31 of the patch pump system 30.

Figure 3A:
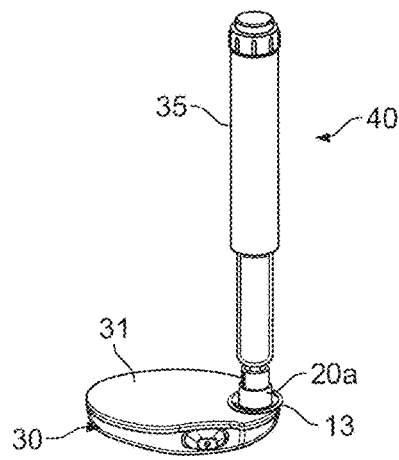
FIG. 3A shows a perspective view of a medicament delivery system coupled to a patch pump system in accordance with some embodiments of the present invention.
Figure 3B:
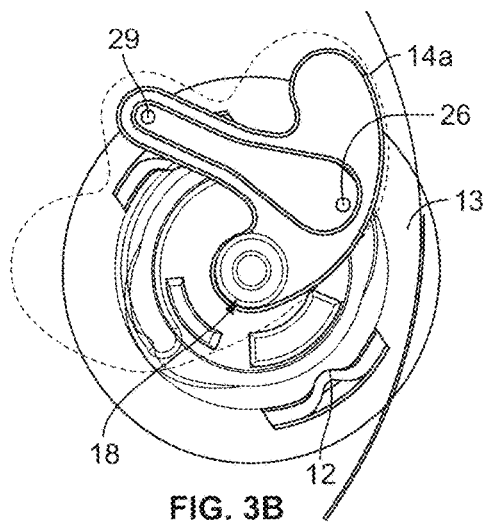
FIG. 3B shows a bottom view of the coupled medicament delivery system of FIG. 3A in which the shutter is in a first closed position in accordance with some embodiments of the present invention.
Figure 3C:
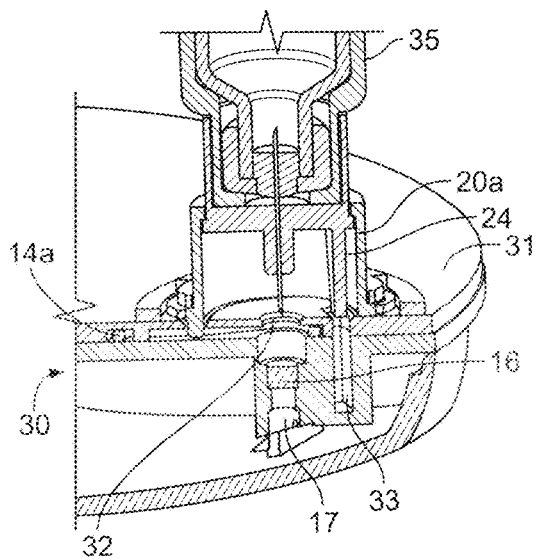
FIG. 3C shows a cross-sectional detail of the coupled medicament delivery system of FIG. 3A in which the shutter is in an open position in accordance with some embodiments of the present invention.
Figure 3D:
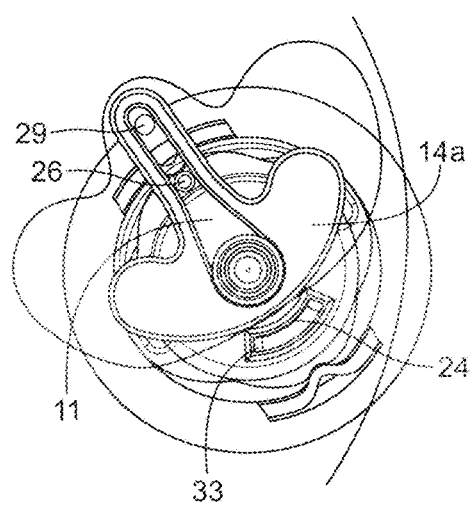
FIG. 3D shows a bottom view of the coupled medicament delivery system of FIG. 3A in which the shutter is in the open position in accordance with some embodiments of the present invention.
Figure 4A:
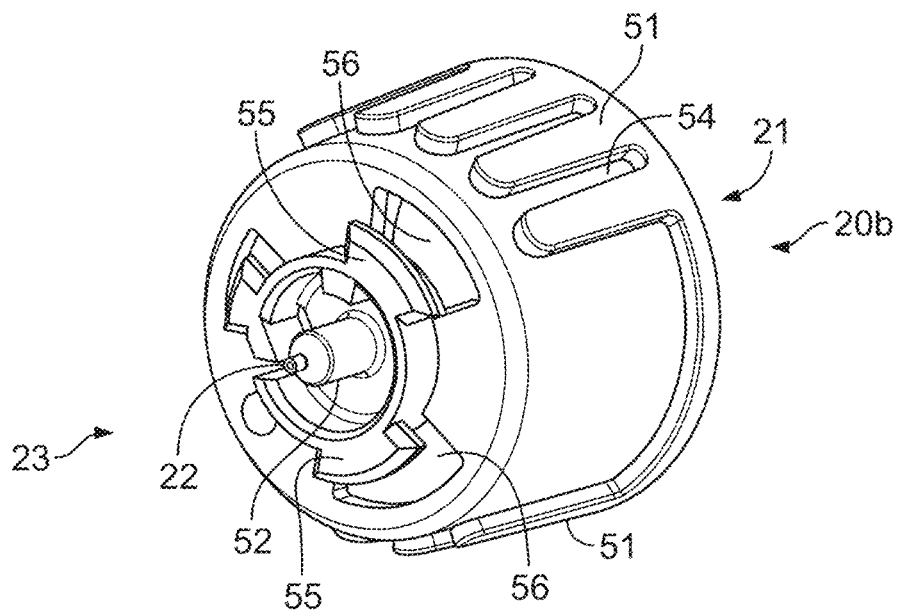
FIGS. 4A and 4B show perspective views of a second adapter key in accordance with some embodiments of the present invention.
Figure 4B:
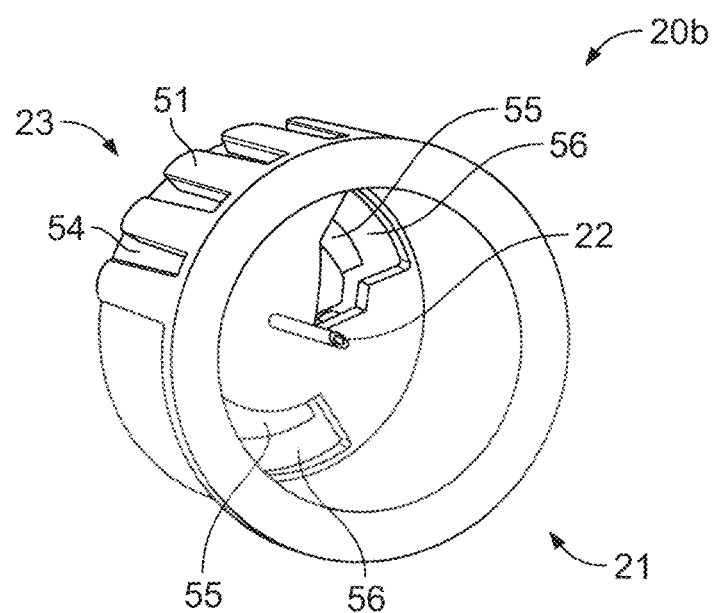

FIGS. 3A-3G illustrate an embodiment of a method of filling the reservoir 17 of a patch pump system 30 using the medicament delivery system 40 described above. In a first step (FIGS. 3A and 3B), the adapter key 20a is inserted into the socket 13 of the patch pump system 30. As shown in FIG. 3B, when the adapter key 20a is first inserted, the shutter 14a is in a closed position, hence, the septum 16 of the reservoir 17 is covered by one of the wings 18 of the T-shaped shutter 14a. In a second step (FIGS. 3C and 3D), the medicament container 35 and the patch pump system 30 and, more specifically, the needle 22 is aligned with the septum 16, in preparation for piercing the septum 16 and for delivery of the medicament. Such alignment can be achieved, for example, by rotation of the medicament container 35 and the adapter key 20a within the socket 13. During rotation, the protrusion 26 on the rim 25 of the adapter key 20a slides along the peripheral wall of the elongate opening 11 of the shutter 14a, urging the shutter 14a such that the proximal end of the elongate opening 11 is aligned with the filling port 32 and the septum 16. Neither wing 18 of the shutter 14a covers the port 32 or septum 16. In one variation, the socket 13 guides and controls rotation and, advantageously, locks the adapter 20a in place, e.g., using the elastic expansion elements 12 and/or a resilient detent, when in the proper position for piercing the septum 16 and for filling the reservoir 17.

With the shutter 14a in an open state (FIG. 3E), in a next step, with the safety protrusion 24 on the first end 21 also aligned with the receptacle 33, the first end 21, slides in an axial direction within the second end 23. The needle 22 is advanced to the delivery position, piercing the septum 16 and allowing for the delivery of medicament to the reservoir 17 in the patch pump device 30. Once the reservoir 17 has been filled with a measured amount of the medicament, the medicament delivery system 40 can be retracted, e.g., by twisting and lifting the medicament container 35 (FIGS. 3F and 3G), to remove and disengage the adapter 20a and medicament container 35 from the patch pump device 30 and to re-close the shutter 14a. As depicted, the container 35 and adapter 20a are twisted past the shutter open position, to cover the port 32 and septum 16 with the second lobe or wing 18 of the shutter 14a. Alternatively, the system 10 could be rotated in the opposite direction to cover the port 32 and septum 16 with the first lobe or wing 18 of the shutter 14a. Advantageously, to prevent additional uses of the adapter 20a, in some variations, certain features, such as the safety protrusion 24, may be frangible so as to break off after filling has been completed, e.g., through twisting while the safety protrusion 24 is contained within the receptacle 33 to the second, re-closed position.

In another embodiment, depicted in FIGS. 4A-7E, a medicament container 35, e.g., a pen, a cartridge, and/or a vial, can be coupled to a first end 21 of a second embodiment of an unique adapter key 20b, which is adapted to receive the medicament container 35, while a second end 23 of the unique adapter key 20b is adapted to mate or couple to a patch pump device 30 via a valve-type shutter 14b. In this embodiment, the shutter 14b may be a valve that is axially rotatable to open or close a fluid path between the needle 22 and the reservoir 17 of the patch pump device 30 when the adapter key 20b and shutter 14b properly aligned. In some implementations, the shutter 14b may have one or more resilient tabs 57, 58 that are designed to deflect more easily in one direction of rotation than another, e.g., for use within a patch pump device 30 having a surrounding ratchet-type configuration 72 (FIGS. 5A, 6A, and 6B). As a result, rotation of the shutter 14b may occur in only one direction, e.g. clockwise, and such rotation, in combination with a ratchet-type configuration, locks or secures the shutter 14b in a desired orientation.

The adapter key 20b (FIGS. 4A and 4B) for the valve-type shutter 14b includes a hollow needle 22 and first end 21 that serve similar purposes as those described in connection with the first embodiment of an adapter key 20*a*. In contrast to the first embodiment, the second end 23 of the adapter key 20*b* is more convex than concave and includes any number of unique interface elements, such as mating male 51, 52 and female portions 54 and openings 56. The interface elements enable the adapter key 20*b* to mate or couple discretely with a valve-type shutter 14*b* and/or with a patch pump device 30 that has an integrated valve-type shutter 14*b* feature, so as to allow the valve-type shutter 14*b* to be rotated within the patch pump device 30, e.g., to align the fluid outlet path 59 with fluid channels leading to the reservoir 17, only when the unique adapter key 20*b* is used. The adapter key 20*b* may also have locking tabs 55 for securing a connection with the patch pump device 30. For example, locking tabs 55 may be used in combination with a bayonet connection 53 (FIG. 7A) formed in the patch pump device 30. Advantageously, these locking tabs 55 may be frangible, so as to break away, e.g., within and while in contact with the bayonet connection 53, after a first use to prevent reuse of the adapter key 20*b*, e.g., by preventing, upon an attempted reuse, a seal for sufficiently pressurizing the medicament for filling the patch pump device 30.

Figure 5A:
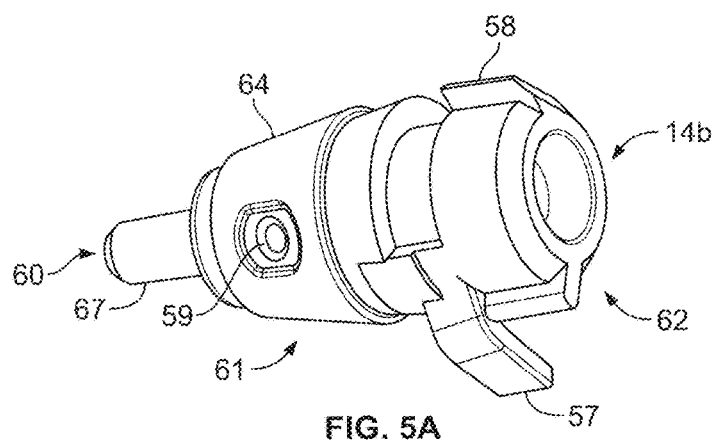
FIG. 5A shows a perspective views of an illustrative embodiment of a valve-type shutter for use with the adapter key of FIGS. 4A and 4B in accordance with the present invention.
Figure 5B:
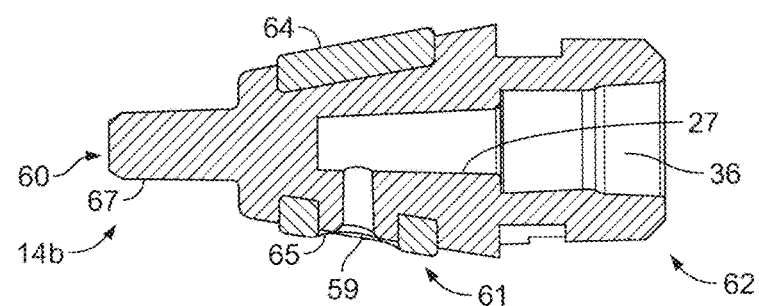
FIG. 5B shows a cross-sectional view of the valve-type shutter of FIG. 5A in accordance with the present invention.

An illustrative embodiment of a valve-type shutter 14*b*, which may be manufactured from a metal, alloy, plastic, and the like, is shown in FIGS. 5A and 5B. The shutter 14*b* includes a distal portion 60, a proximal portion 62, and a central portion 61. The distal portion 60 includes, e.g., a cylindrical or substantially cylindrical nose 67 that is configured to fit snugly into a first recessed portion 10 in the patch pump device 30 to align the shutter 14*b* and needle 22 properly and to provide an axis about which to rotate the medicament delivery system 40. The proximal portion 62 includes a first opening 36 that is dimensioned for receiving, inter alia, a male portion 52 of the adapter key 20*b*, e.g., in a tight, sliding fit, to provide an air- and fluid-tight seal. A plurality of tabs 57, 58 may be formed on the outer surface of the proximal portion 62. The longer tab 57 is configured to fit into a plurality of locations 71, 73, and 74 for the purposes described in detail below.

Figure 5C:
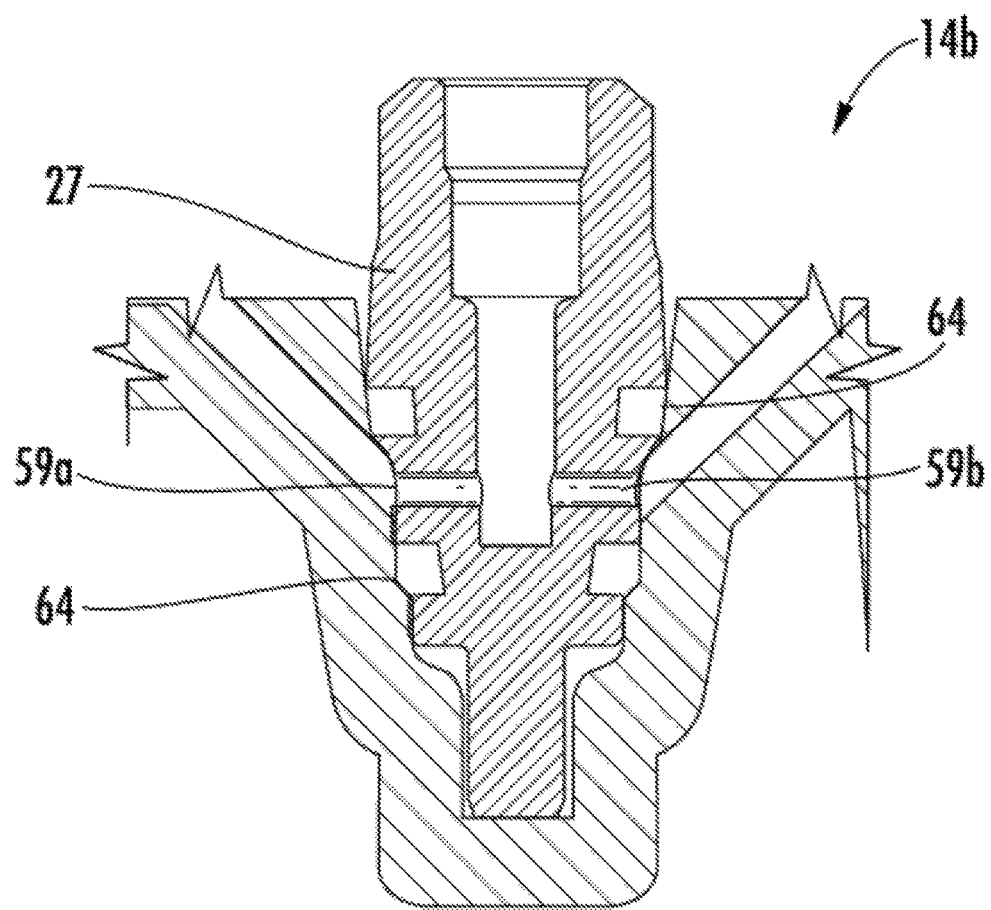
FIG. 5C shows a cross-sectional view of an embodiment of a valve-type shutter having two fluid outlet paths in an open state for use with the adapter key of FIGS. 4A and 4B in accordance with the present invention.

The central portion 61 of the shutter 14*b* includes a recessed portion 27, which is adjacent to and coaxial with the first opening 36 and in fluid communication with a fluid outlet channel 59, and an outer seal 64, e.g., an elastomeric material, silicone, thermoplastic elastomer (TPE), and the like, that is disposed or formed about the periphery of the central portion 61. The recessed portion 27 is dimensioned for receiving, inter alia, the needle 22 and for channeling or communicating medicament from the medicament container 35 into the fluid outlet channel 59. The outer seal 64, which includes an opening 65 that surrounds the fluid outlet channel 59, is adapted to fit snugly against a second recessed portion 34 in the patch pump system 30 to provide an air- and fluid-tight seal around the opening 65 during the filling operation. FIG. 5C shows a variation of the valve-type embodiment, in which the recessed portion 27 is adjacent to and coaxial with the first opening 36 and in fluid communication with multiple fluid outlet channels 59*a*, 59*b*.

In use, when the shutter 14*b* is in a closed configuration (FIG. 7A), a portion of the outer seal 64 other than the opening 65 is disposed between the fluid outlet channel 59 and a fluid port 63 in the patch pump system 30 to prevent premature delivery of the medicament into the patch pump system 30. When the shutter 14*b* is in an open configuration (FIG. 7C), the opening 65 is disposed about and aligned with the fluid outlet channel 59 and the fluid port 63, to provide a fluid path and an air- and fluid-tight seal at the fluid port 63 during the filling operation.

Figure 6A:
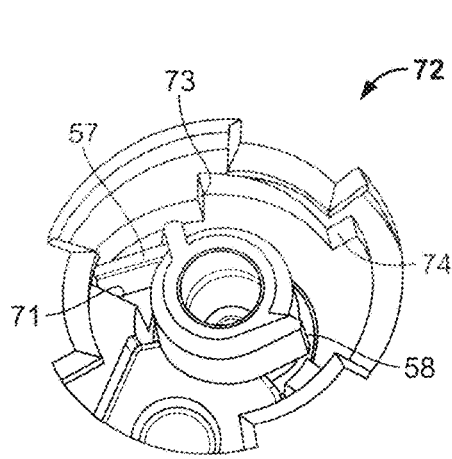
FIG. 6A shows a bottom perspective view of the valve-type shutter disposed at a first location within a ratchet-type system within the patch pump system for use with the adapter key of FIGS. 4A and 4B in accordance with some embodiments of the present invention.
Figure 6B:
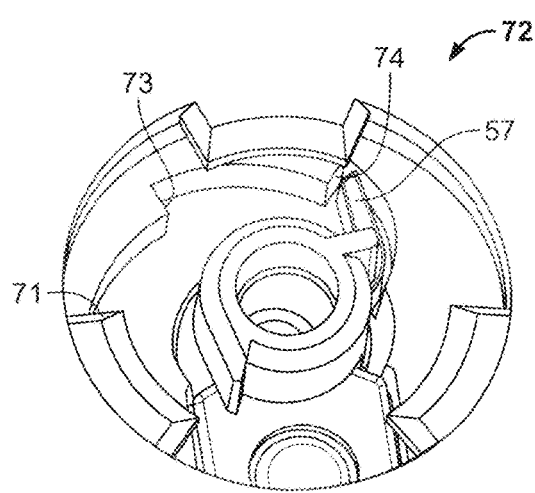
FIG. 6B shows a bottom perspective view of the valve-type shutter disposed at a second location within the ratchet-type system within the patch pump system for use with the adapter key of FIGS. 4A and 4B in accordance with some embodiments of the present invention.
Figure 7A:
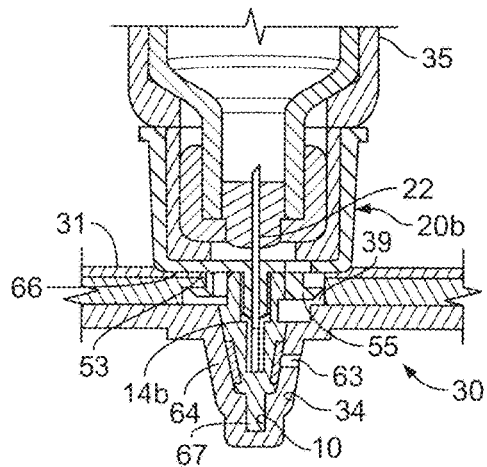
FIG. 7A shows a cross-sectional view of the second adapter key of FIGS. 4A and 4B mounted in the valve-type shutter of FIGS. 5A and 5B in a closed position in accordance with some embodiments of the present invention.
Figure 7C:
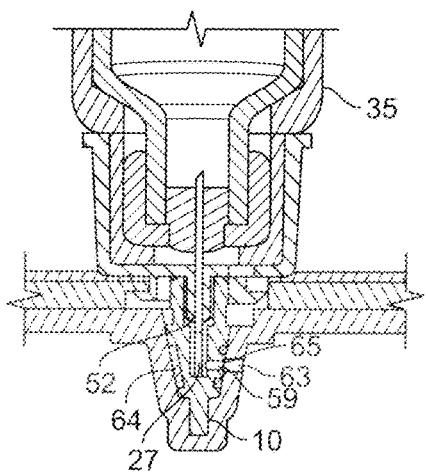
FIG. 7C shows a cross-sectional view of the second adapter key of FIGS. 4A and 4B mounted in the valve-type shutter of FIGS. 5A and 5B in an open position accordance with some embodiments of the present invention.
Figure 7B:
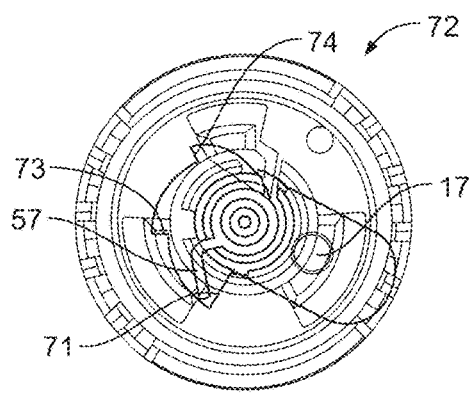
FIG. 7B shows a bottom view of the coupled valve-type shutter and adapter key of FIG. 7A with a resilient tab disposed at a first location within a ratchet-type system of the patch pump system in accordance with some embodiments of the present invention.
Figure 7D:
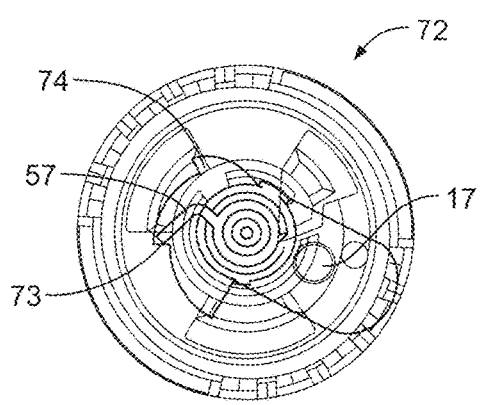
FIG. 7D shows a bottom view of the coupled valve-type shutter and adapter key of FIG. 7C with a resilient tab disposed at a second location within a ratchet-type system of the patch pump system in accordance with some embodiments of the present invention.
Figure 7E:
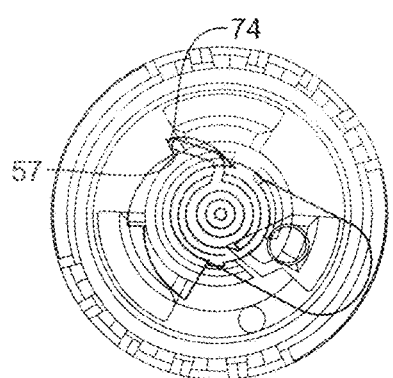
FIG. 7E shows a bottom view of the coupled valve-type shutter and adapter key of FIG. 7A with a resilient tab disposed at a third location within a ratchet-type system of the patch pump system in accordance with some embodiments of the present invention.

FIGS. 7A-7E illustrate an embodiment of a method of filling the reservoir 17 of a patch pump system 30 using the medicament delivery system 40 having the adapter key 20*b* and shutter 14*b* described above. Those of ordinary skill in the art can appreciate that the steps of attaching the adapter key 20*b* to the medicament container 35 may be similar to those described above in connection with FIGS. 2A-2C and, moreover, that the steps of installing the medicament delivery system 40 on the patch pump system 30 may be similar to those described above in connection with FIG. 3A. Other attachment systems can alternatively be used, if desired. Once the adapter key 20*b* and medicament container 35 have been joined to create a fluid communication between the needle 22 and the medicament container 35, in a first step (FIGS. 7A and 7B), the adapter key 20*b* may be inserted into an opening 66 in the patch pump system 30 and rotated, so that the locking tabs 55 engage the bayonet connection 53 formed in the patch pump system 30 at the opening 66. FIGS. 6A, 7A, and 7B shown the system in a closed position, which is to say, the longer tab 57 may be disposed at a first location 71 of the ratchet-type configuration 72. At the first location 71, the longer tab 57 prevents the medicament delivery system 40 from being rotated in a counter direction, e.g., counterclockwise, to the rotation direction, e.g., clockwise, used to lock the locking tabs 55 within the bayonet connection 53. In this state, the outer seal 64 of the shutter 14*b* may be positioned between the fluid outlet channel 59 and the fluid port 63. Hence, no fluid path exists for communicating medicament into the reservoir 17 of the patch pump system 30.

In a next step (FIGS. 7C and 7D), the medicament delivery system 40 may be further rotated until the longer tab 57 reaches the second location 73 of the ratchet-type configuration 72. When the longer tab 57 reaches the second location 73, the system is in an open position. At the second location 73, the longer tab 57 again prevents the medicament delivery system 40 from being rotated in a counter direction. In the open position, the fluid outlet channel 59 and the fluid port 63 are in fluid communication and the outer seal 64 of the shutter 14*b* is positioned, such that opening 65 in the outer seal 64 is disposed about the fluid outlet channel 59 and the fluid port 63, to provide an air- and fluid-tight connection. Thus, a fluid path is now open for transferring medicament from the medicament delivery system 40 into the reservoir 17 of the patch pump system 30.

Finally, in a next step (FIGS. 6B, 7A, and 7E), the medicament delivery system 40 may be further rotated until the longer tab 57 reaches the third location 74 of the ratchet-type configuration 72. When the longer tab 57 reaches the third location 74, the system again is in a closed position. At the third location 74, the longer tab 57 again prevents the medicament delivery system 40 from being rotated in a counter direction. Moreover, the outer seal 64 of the shutter 14*b* is again positioned, such that outer seal 64 is disposed between the fluid channel 59 and the fluid port 35. Hence, the fluid paths are closed to transferring medicament into the reservoir 17 of the patch pump system 30.

Advantageously, to prevent multiple uses of the adapter 20*b*, in some variations, certain features, e.g., the locking tabs 55, may be frangible so as to break off after filling has been completed, e.g., through further twisting. The valve-type shutter 14*b*, however, may be reused and can be properly sanitized to remove any trace of the transferred medicament or contamination.

Figure 8A:
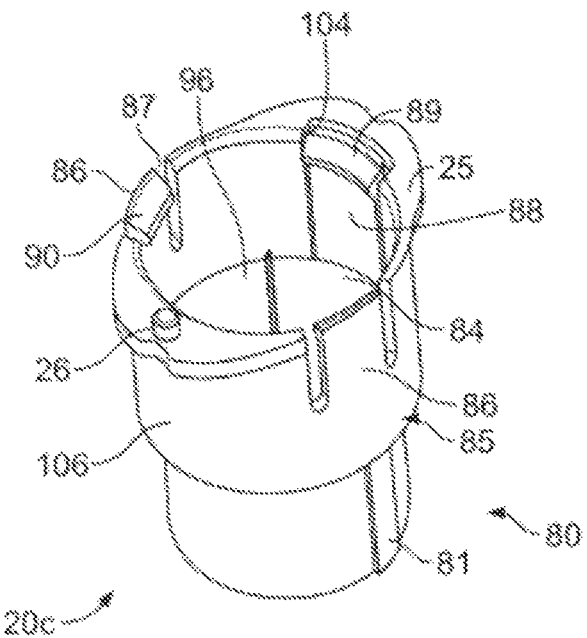
FIG. 8A shows a perspective view of an adapter key for use with a syringe in accordance with some embodiments of the present invention.
Figure 8B:
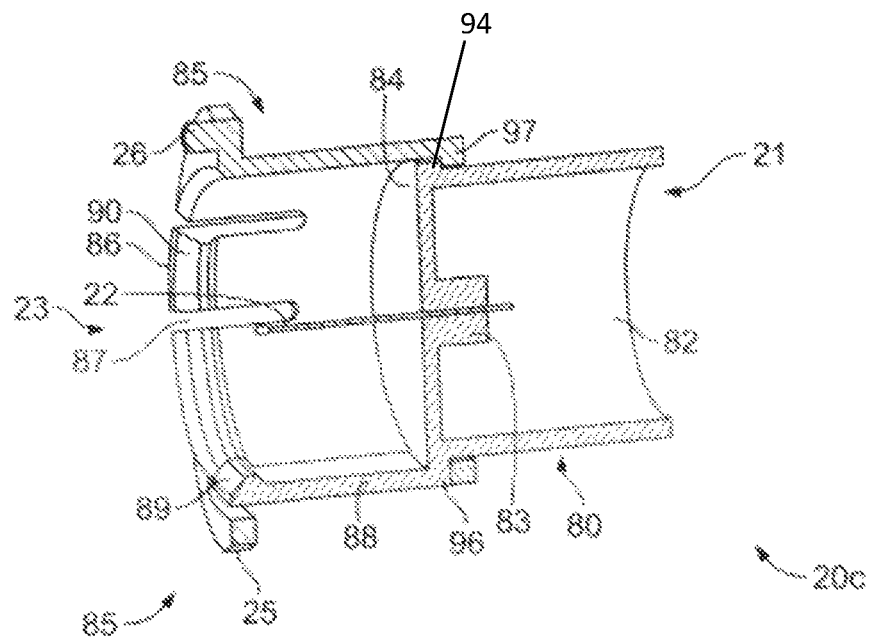
FIG. 8B shows a cross-sectional view of the adapter key of FIG. 8A in accordance with some embodiments of the present invention.

In yet another embodiment, the medicament delivery system 45 may include a syringe 95 as a medicament container instead of a pen, a vial, and/or a cartridge. Referring to FIGS. 8A and 8B, in some implementations, for use with a syringe 95, the adapter key 20c includes a first portion 80 and a second portion 85 that are coaxially arranged with respect to each other, such that first portion 80 may displace co-axially and slidingly within the plenum 96 of the second portion 85. Hence, the outer diameter of the first portion 80 may be slightly smaller than the inner diameter of the second portion 85 to facilitate the axial displacement. The first portion 80 of the adapter key 20c may be configured receive and retain a syringe 95, e.g., by axial pressing and/or twisting, while the second portion 85 of the adapter key 20c may be adapted, first, to receive and retain a medicament vial 99 while filing the reservoir of the syringe 95 with a measured amount of a medicament and, subsequently, may be coupled to the patch pump device 30, e.g., by axial pressing and/or twisting, for filling the reservoir 17 of the patch pump system 30. The first portion 80 and a second portion 85 may be manufactured of metal, an elastomeric material, plastic, rubber, and the like.

The first portion 80 may be cylindrical or substantially cylindrical in shape and may include an open first end 21 and a second end that is closed by a wall 84, defining a plenum 82 within the wall 84 and the circumferential walls of the first portion 80. The wall 84 includes an aperture through which a hollow needle 22, extending into both the plenum 82 of the first portion 80 and the plenum 96 of the second portion 85, is disposed. In some variations, a reinforced area 83 is provided in the vicinity of a needle aperture to provide greater support to the cantilevered needle 22 and to ensure that the needle 22 remains centered and normal or substantially normal to the surface of the wall 84. The wall 84 may disk-shaped and dimensioned to have a diameter that is slightly larger than the outer diameter of the first portion 80 to provide a shoulder 94. The shoulder 94 of the first portion 80 is configured to abut an annular ring 97 of the second portion 85 and to support a cantilevered safety protrusion 88, the purpose of which will be described in detail below. An alignment device 81, which is dimensioned to fit into a groove to track in the second portion 85 and structured and arranged to control the axial sliding of the first portion 80 with respect to the second portion 85, may also be formed on the outer peripheral surface of the first portion 80.

The second portion 85 may be hollow and cylindrical or substantially cylindrical in shape, including an open first and second ends 23, such that, once the first portion 80 of the adapter key 20c has been properly inserted into the hollow second portion 85, the wall 84 of the first portion 80 and the circumferential walls of the second portion 85 produce a plenum 96 within in the second portion 85. A continuous, uninterrupted annular ring 97 may be formed about the entire circumference of the second portion 85 at the open first end. The outer diameter of the annular ring may be dimensioned to be flush with the outer peripheral surface of the circumferential wall of the second portion 85. The thickness and inner diameter of the annular ring 97 are dimensioned to abut the shoulder 94 of the wall 84 of the first portion 80, while allowing the circumferential wall of the first portion 80 to slidingly and axially translate within the plenum 96 of the second portion 85. A groove or track that is dimensioned to receive the alignment device 81 formed on the outer, peripheral surface of the first portion 80 may be included in the annular ring 97 and/or the inner surficial wall of the second portion 85. The groove or track and the alignment device 81 retain the concentric and coaxial first 80 and second portion 85 at a desired orientation with respect to each other during translation of the first portion 80 within the second portion 85.

The circumferential wall 106 of the second portion 85 includes a plurality of, e.g., two, locking tabs 86 and a first opening 104, which is dimensioned to receive the safety protrusion 88 of the first portion 80. The locking tabs 86 are cantilevered sections in the circumferential wall 106 of the second portion 85 and include keyed ends 90. The cantilevered nature of the locking tabs 86, which allows the locking tabs 86 to displace, e.g., elastically, in a radial direction, is provided by forming axially-oriented slits 87 on either side of the locking tab 86. The keyed ends 90 include a projection that protrudes radially inward of the locking tab 86. The safety protrusion 88 is supported by the wall 84 of the first portion 80 and cantilevered to allow the protrusion 88 to displace, e.g., elastically, in a radial direction. The safety protrusion 88 includes a keyed end 89 that includes a projection that protrudes radially inward of the protrusion 88. In some variations, the second end 23 of the adapter key 20c may include a rim 25 having a desired shaped and dimensions and on which a protrusion 26 is formed. Advantageously, the shape and dimension of the rim 25 can be selected to mate or couple with the opening 15 of the socket 13 on the user contact side 31 of the patch pump system 30.

The first end 21 and the first portion 80 of an adapter key 20c may be structured and arranged to receive a syringe 95, while a second end 23 and the second portion 85 of the adapter key 20c may be structured and arranged to receive a medicament vial 99 to fill the reservoir of the syringe 95 with a measured amount of a medicament, as well as to mate with the socket 13 of the patch pump system 30 to provide a lock and key type filling interface. In this manner, access for filling the medicament reservoir or pump 17 of the patch pump system 30 is limited to individuals possessing the adapter key 20c, the manufacture and distribution of which may be suitably controlled to prevent filling the patch pump system 30 with unauthorized or improper medicaments or by unauthorized individuals.

As shown in FIGS. 9A-9D, the embodied keyed medicament delivery system 45 includes a syringe 95 that may be filled with a measured amount of insulin and the unique adapter key 20c previously described. The unique adapter key 20c initially provides a fluidic connection between the syringe 95 and a medicament vial 99 for the purpose of filling the syringe 95 with a measured amount of medicament and, subsequently, provides a fluidic connection between the syringe 95 and the socket 13 of the patch pump device 30 for the purpose of filling the reservoir 17 with the measured amount of a medicament.

As shown in FIGS. 8A and 8B, the hollow needle 22, extending axially in opposing directions about the wall 84, may be contained within the adapter key 20c and may be disposed within the plenums 82, 96 of the first portion 80 and the second portion 85 to protect a user against inadvertent sticking. The first portion 80 and the second portion 85 of the adapter key 20c may be movable with respect to each other, so that the first portion 80, including the needle 22 and the safety protrusion 88 may translate axially within the plenum 96 of the second portion 85. Such relative translation forces the hollow needle 22 through the septum 16 of the filling port 32.

Figure 9A:
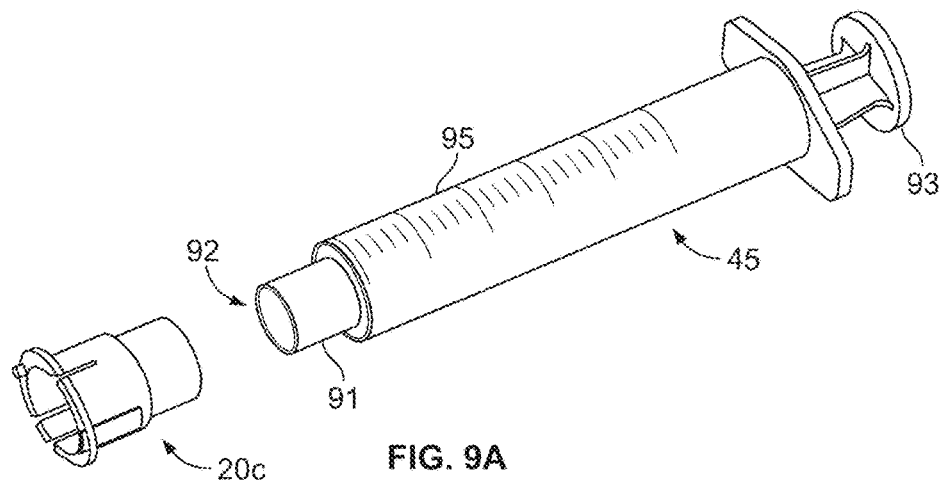
FIGS. 9A and 9B show perspective views of an illustrative embodiment of a syringe-type medicament delivery system having the adapter key of FIG. 8A in accordance with the present invention.
Figure 9B:
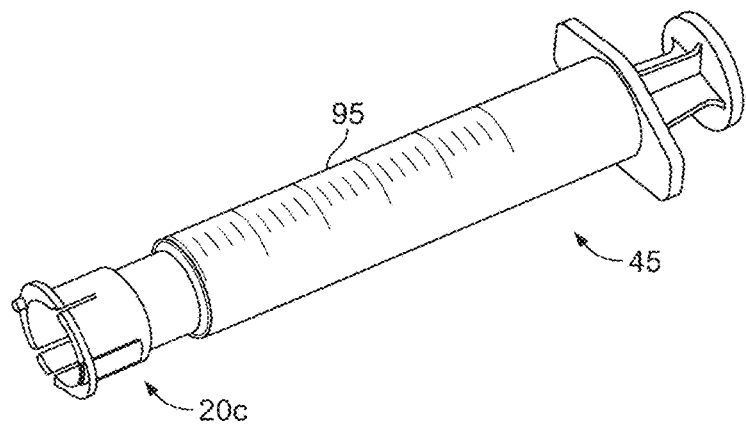

As shown in FIGS. 9A and 9B, the first portion 80 of the adapter key 20c is adapted to mate or couple with a syringe 95 at a first end 92 thereof. In some variations, the first end 92 of the syringe 95 includes a fitting 91 for releasably connecting, e.g., by tight sliding fit, with threadings, and the like, the syringe 95 within the plenum 82 of the first portion 80 at the first end of 21 the adapter key 20c. In some variations, the coupling between the first portion 80 and the first end 92 of the syringe 95 provides an air- and fluid-tight seal, such that, when a syringe piston 93 is retracted from the reservoir of the syringe 95, suction or a negative pressure is produced to draw a measured amount of medicament from a vial 99 through the needle 22 into the reservoir of the syringe 95.

Figure 9C:
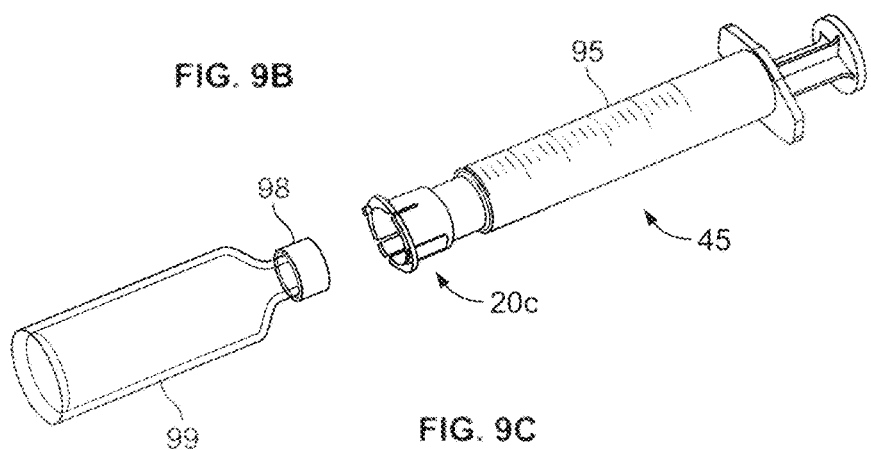
FIGS. 9C and 9D show perspective views of the syringe-type medicament delivery system of FIGS. 9A and 9B and a medicament vial in accordance with the present invention.
Figure 9D:
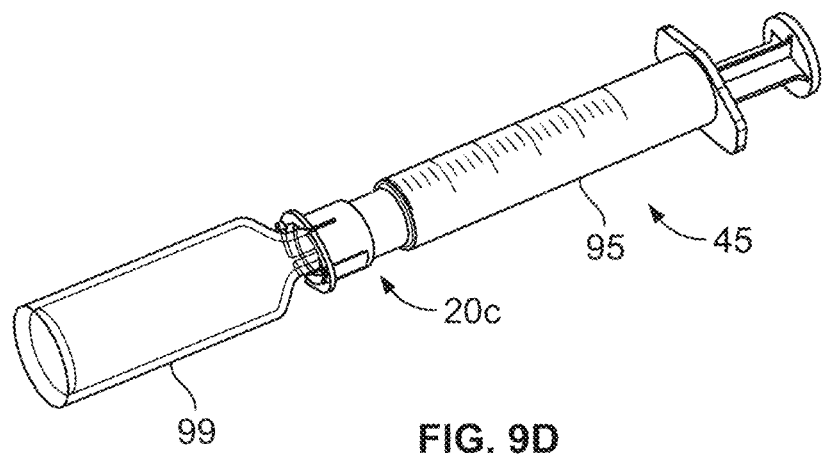
Figure 9E:
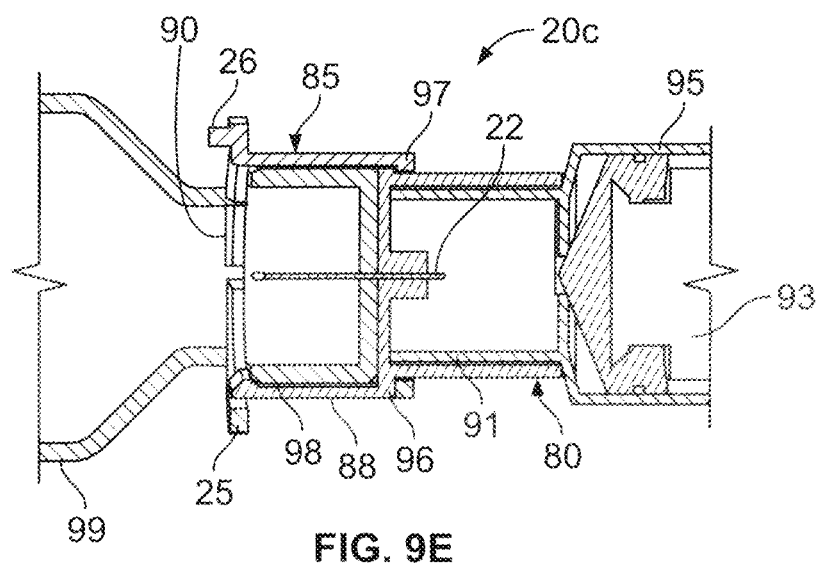
FIG. 9E shows a cross-sectional view of the adapter key of FIG. 8A coupled to a medicament vial of FIG. 9D in accordance with some embodiments of the present invention.

As shown in FIGS. 9C and 9D, the second portion 85 of the adapter key 20c is adapted to mate or couple with a medicament vial 99. In some variations, the medicament vial 99 includes a fitting 98 for releasably connecting with the second portion 85 of the adapter key 20c. More specifically, as shown in FIGS. 9D and 9E, as the second portion 85 of the adapter key 20c is urged over the fitting 98, the protrusions 90 of the locking tabs 86 and the protrusion 89 of the safety protrusion 88 are displaced radially outward away from the needle 22 until the protrusions 89, 90 reach the end of the fitting 98. Once the protrusions 89, 90 have slid or passed over the end of the fitting 98, the hollow needle 22 has established fluidic communication between the medicament vial 99 and the syringe 95. Moreover, the protrusions 89, 90 have been allowed to return, e.g., elastically, at least partially toward their normal or original position. Advantageously, in their normal or original position, the protrusions 89, 90 are able to engage and retain the rim of the fitting 98 during the syringe-filling operation. The syringe piston 93 may then be retracted from the reservoir of the syringe 95, drawing a measured amount of medicament from the medicament vial 99 into the syringe reservoir. Once a desired volume of medicament has been drawn into the reservoir of the syringe 95, the medicament delivery system 45 is ready to fill the reservoir 17 of the patch pump system 30 and may be removed from the medicament vial 99.

Due to the many similarities of the first unique adapter key 20a and the adapter key 20c of FIGS. 9A-9E and FIGS. 10A-10D, the arrangement of the patch pump system 30 and the steps for filling the reservoir 17 of the same may be similar. For example, in some implementations of this embodiment, the patch pump system 30 includes a guiding socket 13, a key-lock filling port 32, and a rotatable shutter 14c that are integrated on or into the user contact side 31 of the patch pump system 30. The socket 13, which may be disposed on the surface of the user contact side 31, is provided as an initial guide for the adapter key 20c. For example, an opening 15 may be formed in the socket 13 and may be shaped and dimensioned to accommodate the outer peripheral surface and/or a rim 25 of the adapter key 20c. In some variations, the socket 13 may also include one or more elastic expansion elements 12 that are structured and arranged to displace radially when the adapter key 20c is inserted into and rotated within the socket opening 15 and oriented to position the shutter 14c in an open or uncovered state.

As previously described, the shutter 14c is provided to cover and uncover a septum 16 that seals the reservoir or pump 17. The shutter 14c may be configured to include a rounded T-shape having a central portion 19 and two wing portions 18. A central, elongate opening 11 adapted to receive a protrusion 26 of the adapter key 20c and a pin 29 about which the shutter 14c may rotate, may be provided in the central portion 19 of the shutter 14c. In some implementations, the shutter 14c is disposed beneath the user contact side 31 of the patch pump system 30 (FIGS. 10A-10D), such that the pin 29 is disposed within a distal end of the elongate opening 11. In operation, the shutter 14c is configured to rotate about the pin 29 upon application of a rotating force or torque to the protrusion 26 of the adapter key 20c. Although the shutter 14c has been described as having a rounded T-shape, those of ordinary skill in the art can appreciate that a myriad of, for example, rounded and polygonal shapes may be used to effect the purpose and function of the shutter 14c. For example, the shutter may be L-shaped, I-shaped, rectangular, triangular, and so forth.

The key-lock filling port 32 includes an opening in the user contact side 31 of the patch pump system 30 and the septum 16, which may be pierced, e.g., by a hollow needle 22, before the reservoir or pump 17 can be filled with a measured amount of medicament. The shutter 14c covers and uncovers the filling port 32, respectively, to protect the septum 16 from and to expose the septum 16 to the needle 22 of the adapter key 20c. In addition to the shutter 14c, the patch pump system 30 may also include a receptacle 33 to provide another degree of security from improper medicament containers 45. For example, the receptacle 33 may be adapted to position the medicament delivery system 45 in a desired location before enabling delivery of a measured amount of medicament and, moreover, is dimensioned to receive a safety protrusion 88 that may be formed in the adapter key 20c. Advantageously, the safety protrusion 88 and receptacle 33 are structured and arranged to mate or couple, so that, only when a proper medicament container 45 is being used can the safety protrusion 88 advance into the receptacle 33, enabling the hollow needle 22 to penetrate the septum 16.

Figure 10A:
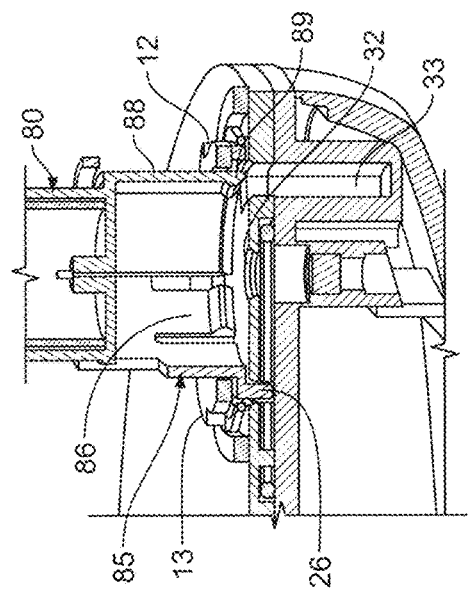
FIG. 10A shows a cross-sectional detail of the medicament delivery system of FIG. 9B and patch pump system with a closed shutter in accordance with some embodiments of the present invention.
Figure 10B:
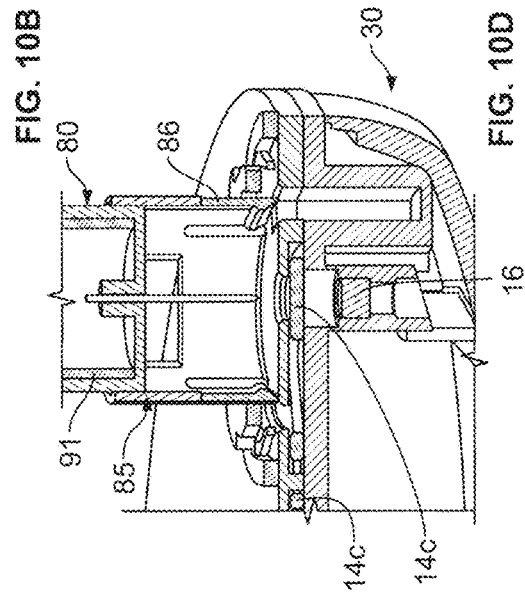
FIG. 10B shows a cross-sectional detail of the medicament delivery system of FIG. 9B and patch pump system with an open shutter in accordance with some embodiments of the present invention.
Figure 10C:
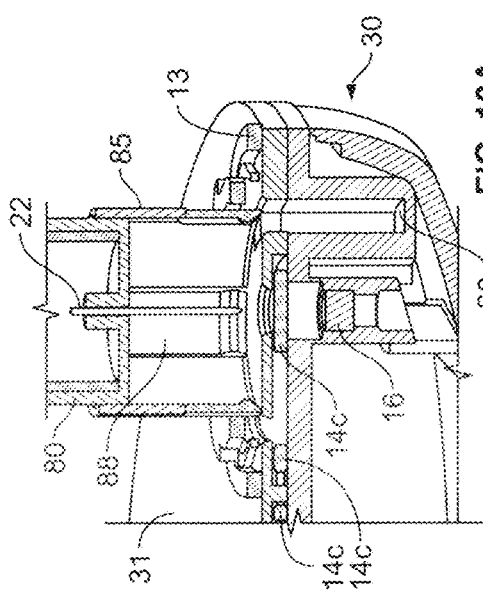
FIG. 10C shows a cross-sectional detail of the medicament delivery system of FIG. 9B in which the needle has pierced the septum of the patch pump system in accordance with some embodiments of the present invention.
Figure 10D:
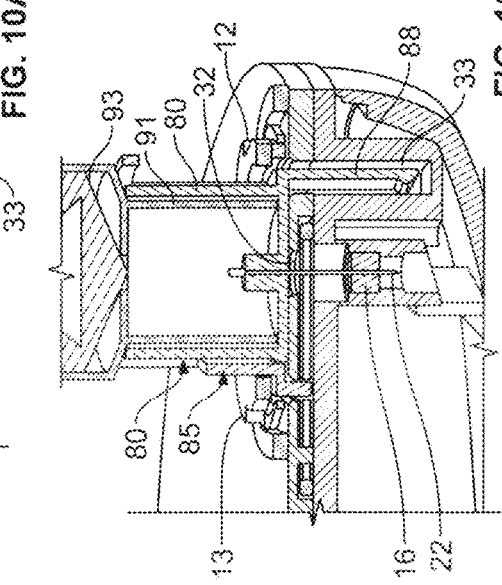
FIG. 10D shows a cross-sectional detail of the medicament delivery system of FIG. 9B and patch pump system in which the shutter is re-closed in accordance with some embodiments of the present invention.
Figure 11A:
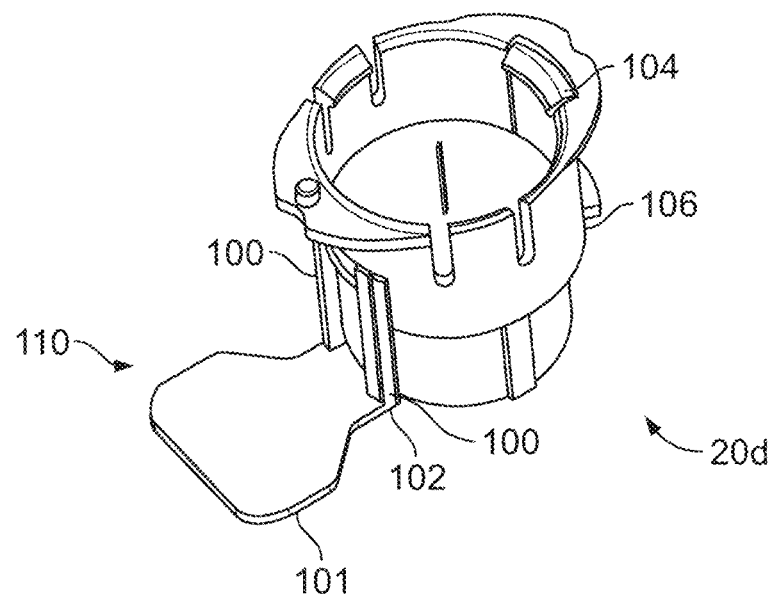
FIG. 11A shows a perspective view of an adapter key with a safety tab for use with a syringe in accordance with some embodiments of the present invention.
Figure 11B:
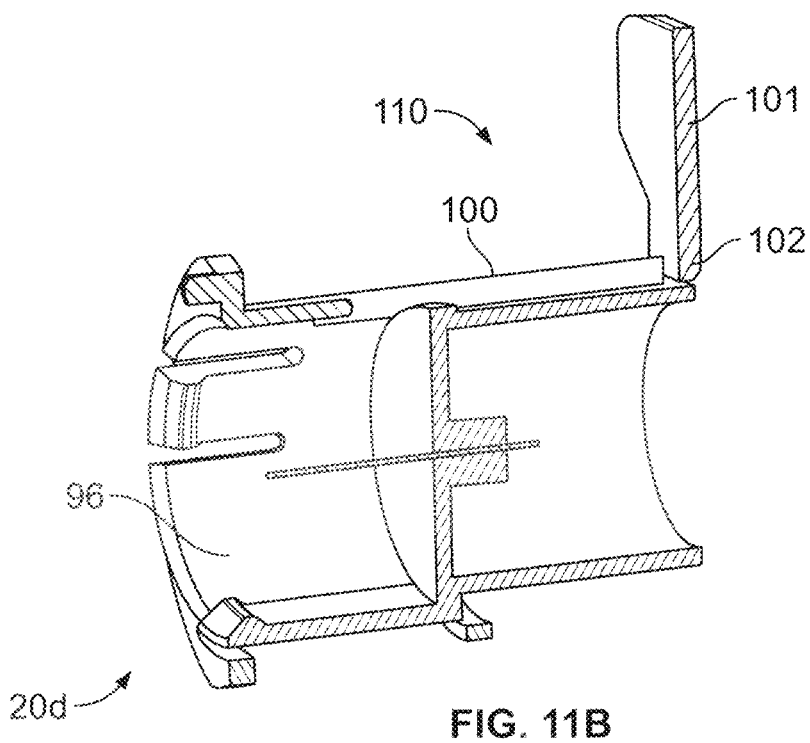
FIG. 11B shows a cross-sectional view of the adapter key of FIG. 11A in accordance with some embodiments of the present invention.

FIGS. 10A-10D illustrate an embodiment of a method of filling the reservoir 17 of a patch pump system 30 using the medicament delivery system 45 described above. In a first step, the adapter key 20c is inserted into the socket 13 of the patch pump system 30. As shown in FIG. 10A, when the adapter key 20c is first inserted, the shutter 14c is in a closed position, hence, the septum 16 of the reservoir 17 is covered by one of the wings 18 of the T-shaped shutter 14c. In a second step (FIG. 10B), the syringe 95 and the patch pump system 30 are aligned for piercing the septum 16 and delivery of the medicament. Such alignment can be achieved, for example, by rotation of the syringe 95 and the adapter key 20c within the socket 13. During rotation, the protrusion 26 on the rim 25 of the adapter key 20c slides along the peripheral wall of the elongate opening 11 of the shutter 14c, urging the T-shaped shutter 14c, such that the proximal end of the elongate opening 11 is aligned with the filling port 32 and/or the septum 16. Neither wing 18 of the shutter 14c covers the port 32 or septum 16. In one variation, the socket 13 guides and controls the rotation and, advantageously, locks the adapter 20c in place, e.g., using the elastic expansion elements 12 and/or a resilient detent, when in the proper position for filling the reservoir 17. Advantageously, when the syringe 95 and the patch pump system 30 the needle 22 and the septum 16 as well as the safety protrusion 88 and the receptacle 33 are properly aligned.

With the shutter 14c in an open state, in a next step (FIG. 10C), once the safety protrusion 88 is aligned with the receptacle 33, the needle 22 can be advanced, e.g., axially, to the delivery position, piercing the septum 16 and allowing for the delivery of medicament to the reservoir 17 in the patch pump device 30. Once the reservoir 17 has been filled, the medicament delivery system 45 can be retracted, e.g., by twisting and lifting the syringe 95, to remove and disengage the adapter 20c and syringe 95 from the patch pump device 30 and to re-close the shutter 14c. As depicted, the syringe 95 and adapter 20c are twisted past the shutter open position, to cover the port 32 and septum 16 with the second wing 18 of the shutter 14c. Alternatively, the system could be rotated in the opposite direction to cover the port 32 and septum 16 with the first wing 18. Advantageously, to prevent additional uses of the adapter 20c, in some variations, certain features, such as the safety protrusion 88, may be frangible so as to break off after filling has been completed, e.g., through twisting while the safety protrusion 88 is contained within the receptacle 33 to the second, re-closed position.

A further variation to the adapter key 20c and medicament delivery system 45 shown in FIGS. 8A through 9B is depicted in FIGS. 11A through 12D. Several of the components and their functional relationships are common to the embodiments of FIGS. 8A through 9B and FIGS. 11A through 12 E, and may be used in a similar manner. One difference to the second portion 85 of the adapter key 20d is the inclusion of a removable safety tab 110 that is structured and arranged to prevent premature deployment of the needle 22 and, thus, exposing the sharp end of the needle 22 while filling the syringe 95 from a medicament vial 99. In some implementations, the removable safety tab 110 is formed on the outer, circumferential wall 106 of the second portion 85 of the adapter key 20d, e.g., diametrically opposed to the aperture 104. In some implementations, the safety tab 110 (FIGS. 11A and 11B) includes a paddle or grip portion 101 and plurality of, e.g., two, elongate legs 100. In some implementations, the paddle portion 101 is perpendicularly or substantially perpendicularly attached to each of the elongate legs 100 at a juncture 102 to form an L shape. The elongate legs 100 are removably attached to the circumferential wall 106 of the second portion 85 of the adapter key 20d and pivotable about corresponding weakened areas 103 in the second portion 85. The elongate legs 100, which extend from the circumferential wall 106 of the second portion 85, are configured to run axially along the peripheral surface of the first portion 80 of the adapter key 20d. More particularly, the elongate legs 100 are axially (longitudinally) dimensioned such that when the first portion 80 of the adapter key 20d is attached to the syringe 95 (FIGS. 12A-12D), the juncture 102 abuts the lip 105 of the syringe 95. Advantageously, such an abutment, retains the sharp end of the needle 22 within the plenum 96 of the second portion 85, preventing exposing the needle 22 prematurely.

Advantageously, while the second portion 85 of the adapter key 20d is attached to the medicament vial 99 (FIG. 12C), as previously described in connection with FIGS. 9C through 9E, the safety tab 110 prevents exposing the needle 22, the abutment afforded by the safety tab 110 does not prevent or hinder the needle 22 from piercing the vial 99 septum or interfere with filling the syringe 95 with a measured amount of medicament. Thereafter, once the medicament vial 99 is removed from the second portion 85 of the adapter key 20d, and before the medicament delivery system 45 is coupled to the patch pump system 30, the tab 110 may be removed from the adapter key 20d, e.g., by rotating the paddle portion 101 about the juncture 102 and/or by pulling the paddle portion 102 towards the weakened sections 103. With some manual twisting and wiggling, the tab 110 should break away from the circumferential wall 106 of the second portion 85 of the adapter key 20d. With the tab 110 removed, as previously describe in connection with FIGS. 10A through 10C, the adapter key 20d, which is now substantially the same as the adapter key 20c, may be mated with or coupled to the socket 13 of the patch pump device 30 and longitudinal advancement of the needle 22 to pierce the septum 16 at the filling port 32 to the medicament delivery position is possible.

Yet another illustrative embodiment of the present invention is depicted in FIGS. 13A through 16F. The patch pump system 30 (FIGS. 15A and 15B) includes a guiding cap 130 (FIG. 13B) that is integrated on or into the user contact side 31 of the patch pump system 30 and an arcuate shutter 14e (FIG. 13A) that also is integrated on or into the patch pump system 30. The arcuate shutter 14e may be disposed beneath the user contact side 31 of the patch pump system 30, so as to open and close the key-lock filling port 32, respectively, to expose and cover the septum 16 to the reservoir 17. Although the invention will be described as having a single arcuate shutter 14e, those of ordinary skill in the art can appreciate that there may be multiple arcuate shutters 14e, e.g., a number less than or equal to the number of resilient tabs 48 on the adapter key 20e. In some implementations, a biasing system, e.g., comprising one or more springs, may bias the arcuate shutter(s) 14e toward the closed position (FIG. 16A). Accordingly, the shutter(s) 14e would require a constant, greater opposing force to remain in the open position (FIG. 16C), which can be provided by the adapter key 20e.

Figure 13A:
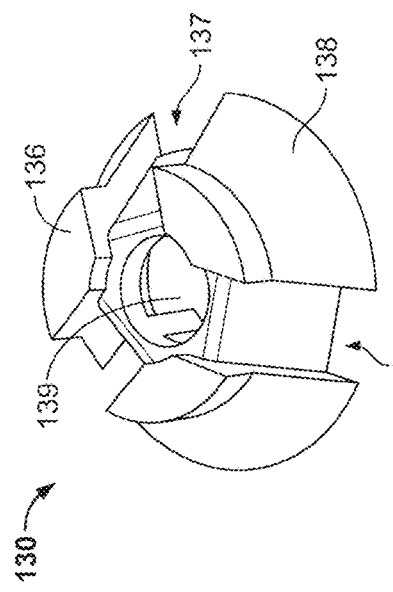
FIG. 13A shows a perspective view of an arcuate shutter for use with another medicament delivery system in accordance with some embodiments of the present invention.
Figure 13C:
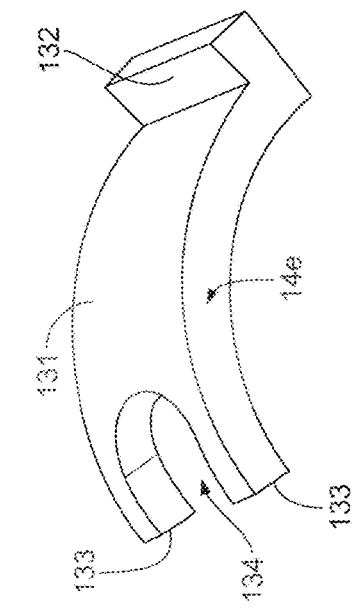
FIG. 13C shows a perspective view of an adapter key for use with another medicament delivery system in accordance with some embodiments of the present invention.
Figure 13B:
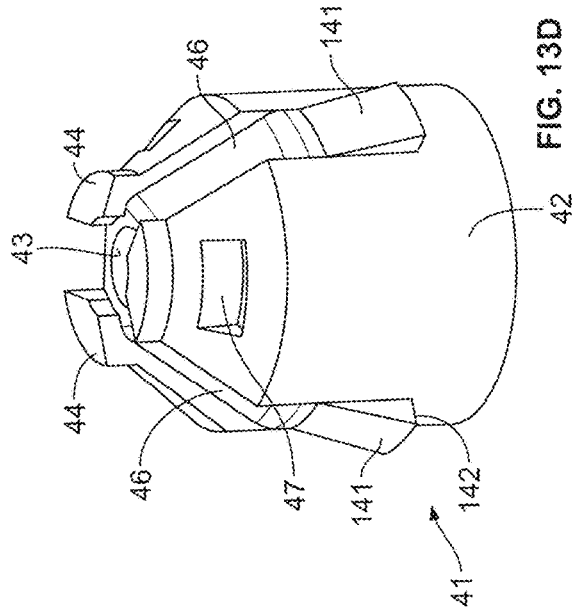
FIG. 13B shows a perspective view of a socket in accordance with some embodiments of the present invention.
Figure 13D:
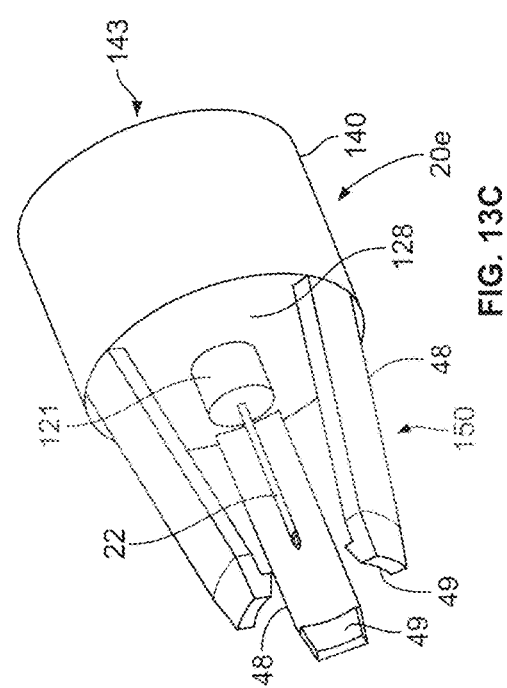
FIG. 13D shows a perspective view of a cap for a medicament vial for use with another medicament delivery system in accordance with some embodiments of the present invention.

The cap 130 (FIG. 13B), which may be disposed on or integrated into the surface of the user contact side 31, is provided as an initial guide for the adapter key 20 e (FIG. 13C). For example, the cap 130, e.g., made of a hard plastic and the like, may be shaped and dimensioned to accommodate a plurality of resilient tabs 48 that are formed on a second portion 150 of the adapter key 20 e. In some variations, the cap 130 is hollow with a conical or frusto-conical shape that includes a plurality of raised portions 136 that project, e.g., in an axial direction, from a base portion 138 and a plurality of cut-out portions 137 that cut into the base portion 138. In some variations, the cut-out portion 137 and the raised portion 136 alternate about the periphery of the cap 130. Although the cap 130 is being described as having a conical or frusto-conical shape, that is done for illustrative purposes only, as the cap 130 could assume any practical shape. Advantageously, the cap 130 includes a centrally located opening 139 that passes through the entire cap 130 and that enables the needle 22 to access the septum 16, as will be described in greater detail below. Each of the cut-out portions 137 is dimensioned to receive and to accommodate a corresponding resilient tab 48 formed in the adapter key 20 e. More particularly, each of the cut-out portions 137 is configured to align with a corresponding opening 119 (FIGS. 16C and 16E) formed in the user contact side 31 of the patch pump system 30. The openings 119 are adapted to position the medicament delivery system 45 in a desired location before delivering the measured amount of medicament.

Figure 14A:
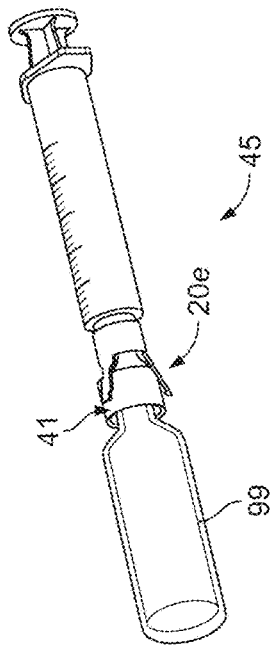
FIG. 14A shows a perspective view of a medicament delivery system with the adapter key of FIG. 13C in accordance with some embodiments of the present invention.
Figure 14B:
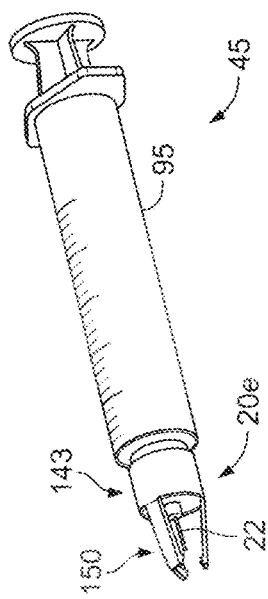
FIG. 14B shows a perspective view of the medicament delivery system of FIG. 14A coupled to a medicament vial in accordance with some embodiments of the present invention.
Figure 14C:
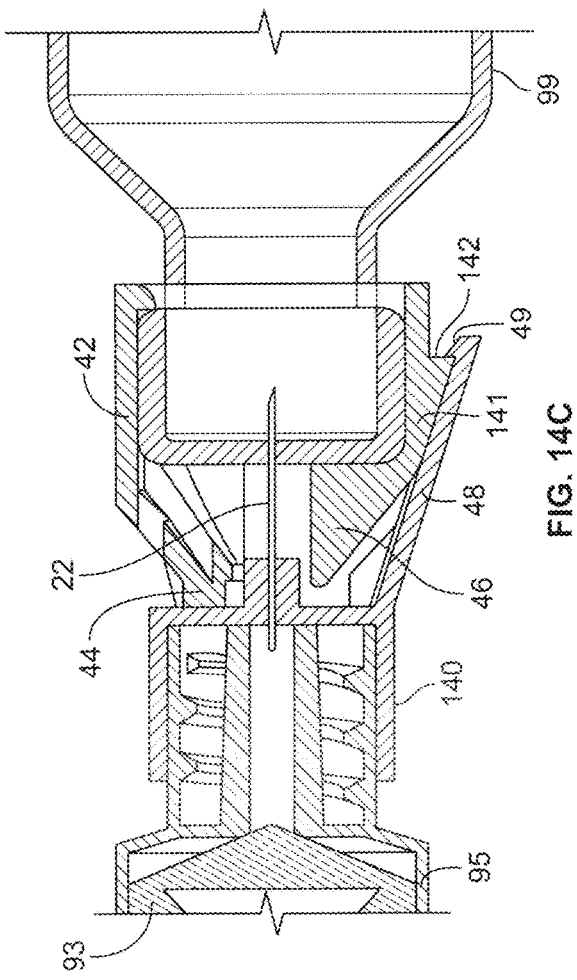
FIG. 14C shows a cross-sectional view of the adapter key of FIG. 13C coupled to a medicament vial in accordance with some embodiments of the present invention.

As shown in FIGS. 14A and 14B, the medicament delivery system 45 includes a medicament container, e.g., a syringe 95 that can be filled with a measured amount of insulin, and an adapter key 20e that is structured and arranged to mate or couple with the guide cap 130 and to provide a fluidic connection between the syringe 95 and a reservoir 17 in the patch pump device 30, for the purpose of filling the reservoir 17 with a measured amount of a medicament. As shown in FIG. 13C, in some implementations, the adapter key 20e includes a first portion 143 and a second portion 150, which are separated by a wall 128 through which an aperture for a needle 22 is formed. To provide greater stiffness to the cantilevered needle 22, a built-up portion 121 may be provided on at least one side of the aperture, e.g., on the first portion 143 side or the second portion 150 side of the wall 128. The hollow needle 22, which is disposed in the aperture in the wall 128 and extends axially in opposing directions, may be surrounded by a plurality of resilient tabs 48 in the second portion 150 and by a circumferential wall 140 in the first portion 143 of the adapter key 20e to protect a user against inadvertent sticking.

The first portion 143 of the adapter key 20e is structured and arranged to mate or couple with a medicament container, e.g., a syringe 95, while filling the syringe 95 from a vial 99 and while delivering a measured amount of medicament to the reservoir 17 in the patch pump system 30. In some variations, the first portion 143 includes a circumferential wall 140 that, with the wall 128, defines a plenum space in the first portion 143. The plenum space and the circumferential wall 140 enable releasably connecting, e.g., by sliding fit, with threadings and the like, the adapter key 20e to the syringe 95. The second portion 150 of the adapter key 20e is structured and arranged to mate or couple with a medicament container 99, e.g., a medicament vial, for the purpose of filling the syringe 95 with a measured volume of medicament; to mate or couple with the guide cap 130 of the patch pump system 30; and to move the arcuate shutter(s) 14e, so as to expose the septum 16 to the reservoir 17 to the needle 22. Unlike previous embodiments, rotation of the medicament delivery device 45, once it has been properly mated with the guide cap 130 on the patch pump system 30, is not necessary.

In some implementations, in order to fill the syringe 95, a special vial cap 41 (FIG. 13D) for connecting the medicament delivery system 45 to the medicament vial 99 is needed. At one end, the cap 41 resembles the guide cap 130, while the other end includes a skirt 42 that is dimensioned to accommodate the syringe 95. In some variations, the vial cap 41 is hollow having, at the first end, a conical or frusto-conical shape that includes a plurality of raised portion 44 and a plurality of cut-out portions 46 that alternate about the periphery of the cap 130. Although the vial cap 41 is being described as having a conical or frusto-conical shape, that is done for illustrative purposes only, as the cap 41 could assume any practical shape. The vial cap 41 includes a centrally located opening 43 that passes through the entire cap 41, for enabling the needle 22 to have access to the septum of the medicament vial 99. Each of the cut-out portions 46 is dimensioned to receive and to accommodate a corresponding resilient tab 48. In some variations, one end of each cut-out portion 46 includes a wedge 141 that is structured and arranged to temporarily catch and hold, e.g., along a stop 142, the locking tabs 49 formed on the end of each of the resilient tabs 48.

In operation, the resilient tabs 48 of the adapter key 20e are aligned with the cut-out portions 46 of the vial cap 41 before the adapter key 20e is urged in an axial direction towards the medicament vial 99. As the resilient tabs 48 ride along the cut-out portions 46, the tabs 48 are displaced radially outward, until the resilient tabs 48 reach the end of the wedge 141, at which point the locking tabs 49 engage or abut the stop 142. With the locking tabs 49 abutting the stop 142, the needle 22 will have pierced the septum of the medicament vial 99, to provide fluid communication between the medicament vial 99 and the syringe 95. Refraction of the plunger 93 of the syringe 95 creates a suction or negative pressure, drawing a measured amount of the medicament into the syringe 95.

The arcuate shutter 14e is provided to cover and uncover the septum 16, which, respectively, interrupts and provides a fluid communication with the reservoir or pump 17. As shown in FIG. 13A, the arcuate shutter 14e may be configured to include an L-shaped end 132 at one, e.g., a distal, end; a U-shaped, e.g., proximal, end; and an arcuate central portion 131 therebetween. In some variations, the U-shaped end includes a pair of legs 133 separated by an opening 134. In some implementations, the shutter 14e is disposed beneath the user contact side 31 of the patch pump system 30, such that in an at rest state, the arcuate central portion 131 of the arcuate shutter 14e is beneath the filling port 32, covering the septum 16.

Figure 15B:
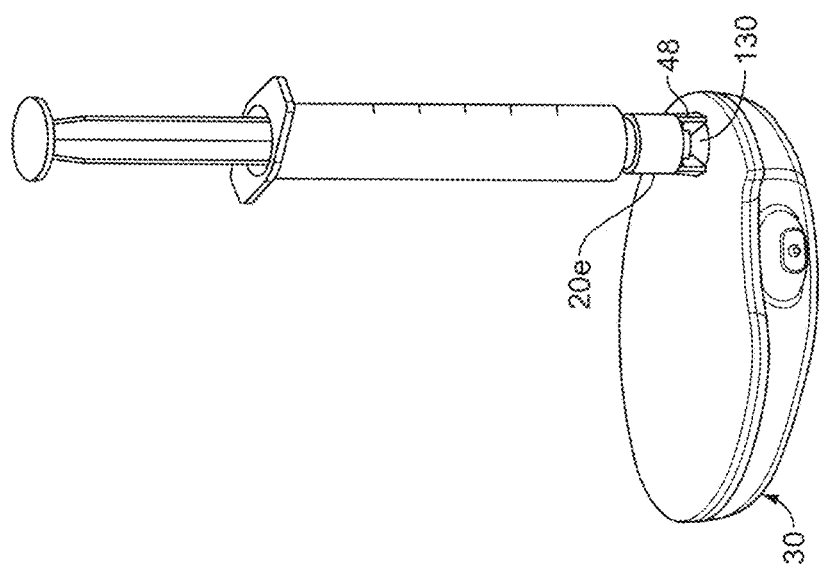
FIG. 15B shows a perspective view of the medicament delivery system of FIG. 14A coupled with the socket of a patch pump system in accordance with some embodiments of the present invention.
Figure 15A:
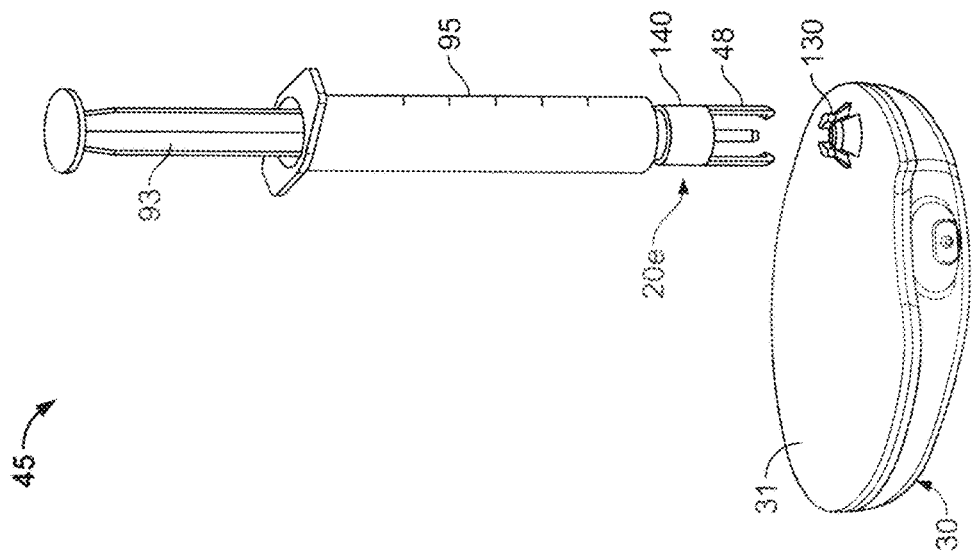
FIG. 15A shows a perspective view of the medicament delivery system of FIG. 14A aligned over the socket of a patch pump system in accordance with some embodiments of the present invention.
Figure 16D:
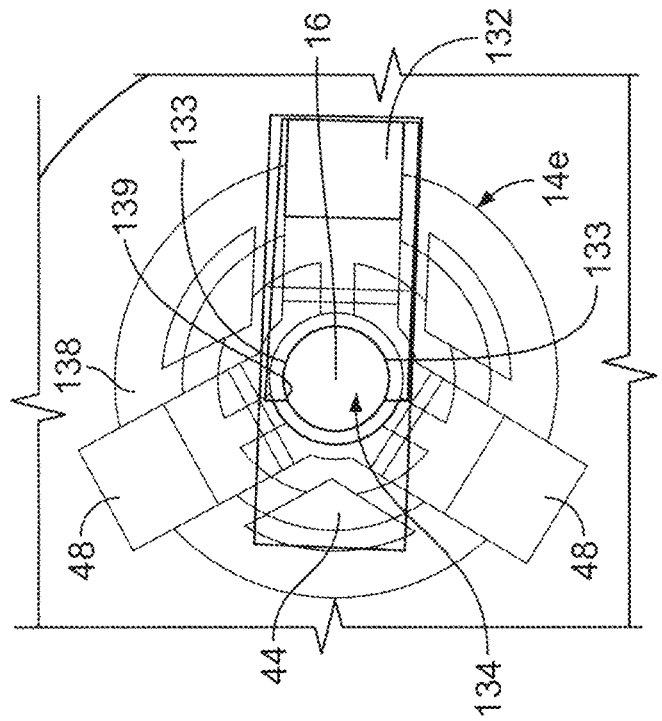
FIG. 16D shows a bottom view of the coupled shutter and adapter key of FIG. 16C in accordance with some embodiments of the present invention.
Figure 16C:
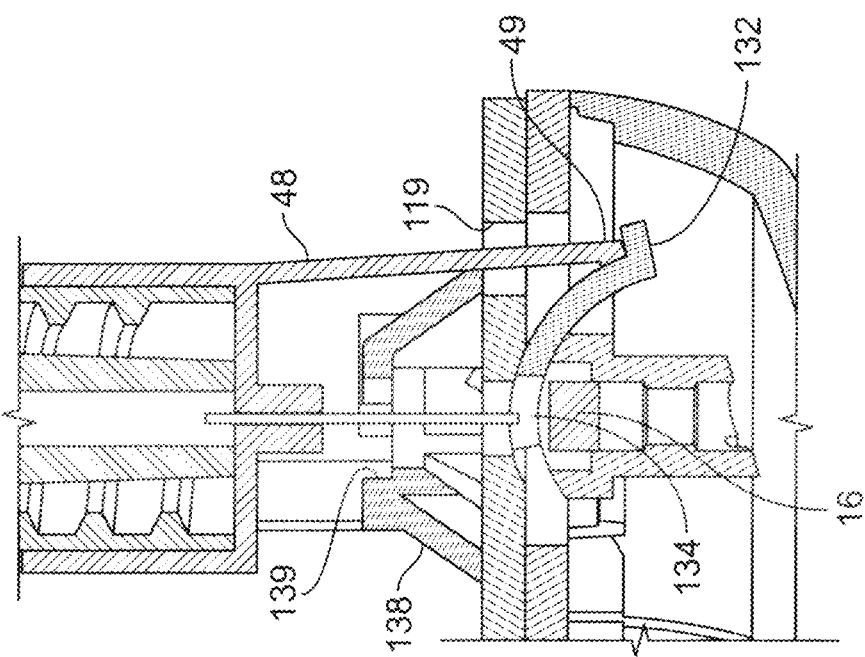
FIG. 16C shows cross-sectional detail of the coupled medicament delivery system of FIG. 15B with the arcuate shutter in an open position in accordance with some embodiments of the present invention.

FIGS. 15A and 15B illustrate an embodiment of a method of mating or coupling a medicament delivery system 45 having adapter key 20e with the guide cap 130 of a patch pump system 30, while FIGS. 16A through 16F illustrate an embodiment of a method of filling the reservoir 17 of the patch pump system 30, using the medicament delivery system 45 having adapter key 20e. In a first step (FIGS. 15A and 15B), the adapter key 20e is inserted into the guide cap 130 of the patch pump system 30, such that each of the resilient tabs 48 of the adapter key 20e are aligned with a corresponding cut-out portion 137 in the guide cap 130, as well as with the openings 119 in user contact surface 31 of the patch pump system 30. As shown in FIGS. 16A and 16B, when the adapter key 20e is first inserted and properly mated in the guide cap 130, one or more of the resilient tabs 48 is positioned above a corresponding opening 119, as well as above the L-shaped end 132 of the arcuate shutter 14e. In this position, the arcuate shutter 14e is in a closed position, such that the central portion 131 of the arcuate shutter 14e covers the septum 16 of the reservoir 17. The needle 22 and the covered septum 16 are properly aligned for delivery of the medicament. In a second step (FIGS. 16C and 16D), the medicament delivery system 45 may be urged further into the patch pump system 30, such that each resilient tab 48 passes through a corresponding opening 119 and, at least one of the resilient tabs 48 contacts the L-shaped end 132 of the arcuate shutter 14e. Further urging of the medicament delivery system 45 displaces the arcuate shutter 14e to an open position, aligning the U-shaped opening 134 and the filling port 32 and exposing the septum 16 to the needle 22.

With the arcuate shutter 14e now open (FIG. 16C), the needle 22 can be advanced, e.g., with further urging of the medicament delivery system 45, to the delivery position in a next step (FIGS. 16E and 16F), that pierces the septum 16 and enables delivery of medicament into the reservoir 17 in the patch pump device 30. Once the reservoir 17 has been filled, the medicament delivery system 45 can be retracted, e.g., by lifting the syringe 95, to remove and disengage the adapter 20e from the guide cap 130 of the patch pump device 30 and to re-close the arcuate shutter 14e. Advantageously, to prevent additional uses of the adapter 20e, in some variations, certain features, e.g., the resilient tabs 48, may be frangible so as to break off after filling has been completed, e.g., by twisting the medicament delivery system 45 to cause the resilient tabs 48 to break against the peripheral surface of openings 119.

Figure 18:
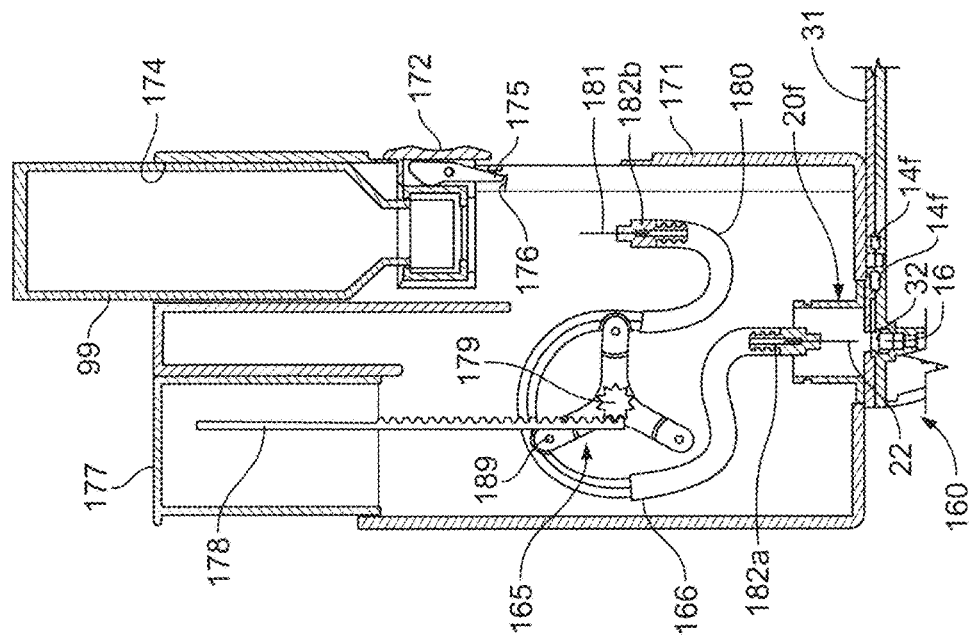
FIG. 18 shows a cross-sectional view of the coupled medicament delivery system of FIG. 17 in a closed position and having a medicament vial attached in accordance with some embodiments of the present invention.
Figure 17:
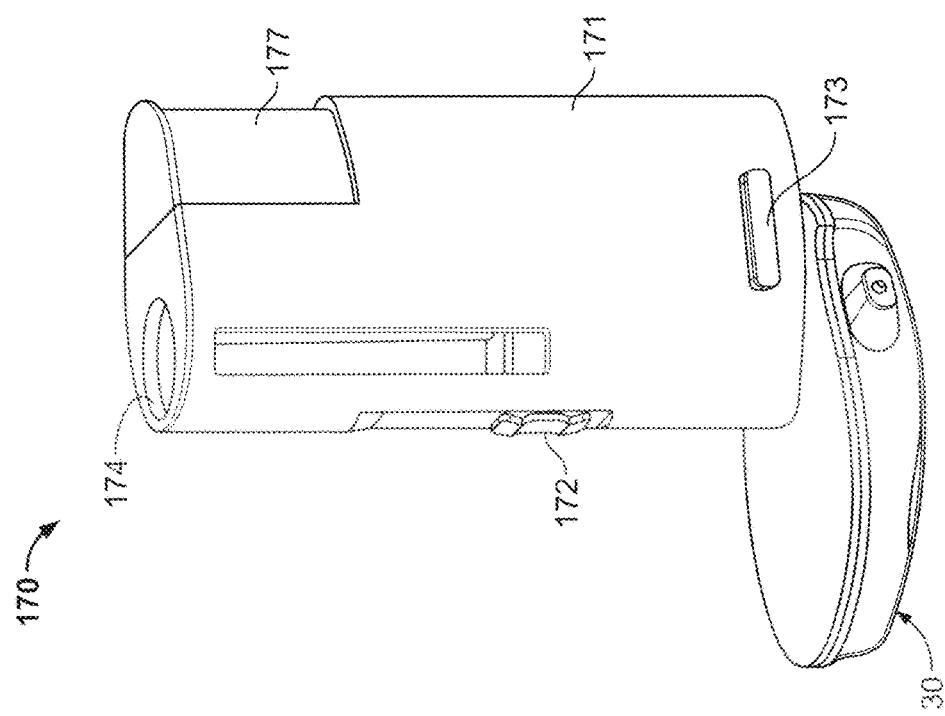
FIG. 17 shows a perspective view of a contained medicament delivery system coupled with a patch pump system in accordance with some embodiments of the present invention.
Figure 19:
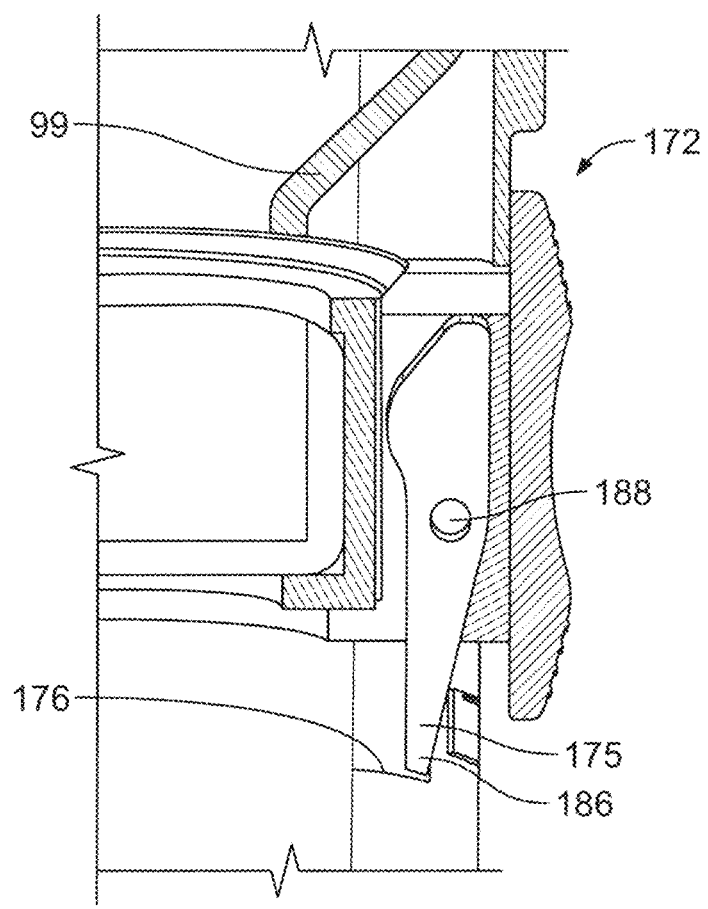
FIG. 19 shows a cross-sectional detail of an activating pin of the contained medicament delivery system of FIG. 17 in accordance with some embodiments of the present invention.

In still another embodiment, an implementation of a self-contained medicament delivery system 170 is depicted in FIGS. 17 through 19. The self-contained medicament delivery system 170 includes a unique adapter key 20f that is disposed at an outlet 160 of the system 170 and adapted to mate or couple with the socket on the user contact side 31 of the patch pump system 30. The adapter key 20f and socket, as well as the corresponding shutter 14f integrated into the patch pump system 30, may be of a type discussed hereinabove and, as a result will not be discussed in further detail.

In some variations, the medicament delivery system 170 (FIG. 17) further includes a housing 171, an inlet 174, for receiving a medicament container, e.g., a medicament vial 99; an outlet 160 that includes a removable or replaceable adapter key 12f; a latch 172, for selectively coupling the medicament container 99 to a second needle 181, and a pump actuation button 177.

Internally, in some variations, the system 170 includes at least one conduit 180, e.g., sterile tubing and the like, and a pump, e.g., a peristaltic pump, mechanism 165 for delivering a measured amount of a medicament, e.g., about 0.2 mL of insulin per actuation of the button 177, into the reservoir 17 of the patch pump system 30. For example, in some applications, the conduit 180 is arranged in a serpentine configuration having a looped portion. The embodied pump mechanism 165 includes a gear-driven rotor 179 having a plurality of, e.g., three, rollers 189 disposed at the ends of a corresponding plurality of rotor arms, and an elongate rack 178 having a plurality of teeth. As shown in FIG. 18, when a user presses down on the pump activation button 177, e.g., using her thumb or other digit, the rack 178 translates linearly in the same direction as the applied force, causing the rotor 179 to rotate.

The operation of a peristaltic pump 165 is well known to those skilled in the art; accordingly, it will only be described briefly in the context of the present invention and use. In short, as the rotor 179 of the gear-driven peristaltic pump 165 rotates, a leading (in the direction of rotation) roller 189 pinches off a leading portion of the flexible, fluid-filled conduit 180. As the leading roller 189 continues to move, a trailing roller 189 pinches off a second, trailing portion of the flexible, fluid-filled conduit 180, confining or trapping a measured volume of the fluid, e.g., 2 mL, between the leading and trailing rollers 189. The leading and trailing rollers 189 continue to rotate with a measured volume of fluid trapped between therebetween. Once the leading roller 189 reaches a pre-determined location 166, it no longer pinches the flexible, conduit 180 and the trailing roller 189 forces the fluid out of the conduit 180 and into the needle 22 and the reservoir 17. Each pump event initiated by depressing the pump actuation button 177 delivers a pre-determined amount of medicament to the reservoir 17, e.g., with about 0.2 mL of insulin.

Needle-carrying fixtures 182a, 182b are removably attached at either end of the conduit 180, e.g., to provide an air- and fluid-tight sliding fit with the conduit 180. A first fixture 182a is translatably disposed within the adapter key 20f and configured, upon activation of the needle deployment device 173, to introduce a needle 22 through the filling port 32 and the septum 16 to provide a fluid communication to the reservoir 17 of the patch pump system 30. A second fixture 182b is disposed in the vicinity of the inlet 174 and latch 172 and configured, upon activation of the latch 172, to urge the septum covering the medicament vial 99 around the needle 181 to provide a fluid communication. More specifically, activation of the latch 172 (FIG. 19) causes the toggle 175 to rotate about a pin 188, such that a distal tip 186 of the toggle 175 clears a shelf 176 that otherwise retains the distal tip 186, preventing the medicament vial 99 from moving. Once the distal tip 186 of the toggle 175 clears a shelf 176, the medicament container 99 is able to slide into contact with a second needle 181.

In some embodiments, the filling pump device 170 is shipped attached to the patch pump device 30, including sterile tubing connecting to the patch pump device 30 at the outlet 160 and to a medicament container 99 at the inlet 174. A counter can also be included to keep track of the filling amount. For example, in one implementation, the counter may count the number of rotations of the rotor 179 of the gear-driven peristaltic pump 165, realizing that the volume of medicament contained within the sterile tubing, between the leading and trailing rollers 189 rotates, is substantially constant, e.g., 2 mL. For the illustrated implementation, one rotation of the rotor 179 would deliver three measured quantities of the medicament or 6 mL to the reservoir 17 of the patch pump device 30.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A patch pump system comprising:
  a patch pump device comprising:
    a filling port, and
    a shutter proximate the filling port movable about a pin between a closed position and an open position and adapted to prevent access to the filling port in the closed position, wherein the shutter comprises:
      a central portion and at least one wing portion extending therefrom, wherein the at least one wing portion is configured to prevent access to the filling port in the closed position, and
      an opening disposed in the central portion, wherein the opening is configured to receive the pin therein; and
    a filling adapter configured to be locked to the filling port and to move the shutter from the closed position to the open position, wherein the filling adapter comprises:
      a first portion and a second portion,
      a rim disposed about the second portion, and
      a protrusion disposed on the rim, wherein the protrusion is configured to engage the opening of the central portion of the shutter to rotate the shutter about the pin from the closed position to the open position upon rotation of the filling adapter.

2. The patch pump system of claim 1, wherein the filling port comprises a septum.

3. The patch pump system of claim 1, wherein the filling port is accessible from a user contact side of the patch pump device.

4. The patch pump system of claim 1, wherein the shutter is accessible from a user contact side of the patch pump device.

5. The patch pump system of claim 1, wherein the shutter is disposed within the patch pump device.

6. The patch pump system of claim 1, wherein the shutter is disposed within the filling port.

7. The patch pump system of claim 1, wherein the shutter defines a shutter opening.

8. The patch pump system of claim 1, wherein the shutter is a valve.

9. The patch pump system of claim 1, wherein the patch pump device defines a device opening for coupling the filling adapter to the filling port and enabling controlled rotation of the shutter.

10. The patch pump system of claim 1, wherein the filling adapter comprises a hollow needle.

11. The patch pump system of claim 1, wherein a first end of the filling adapter is adapted to mate with a medicament container.

12. The patch pump system of claim 1, further comprising a socket adapted to receive the filling adapter.

13. The patch pump system of claim 1, wherein the second portion is coaxially arranged with respect to the first portion, and wherein the first portion is slidingly displaceable within the second portion.

14. The patch pump system of claim 13, wherein the filling adapter comprises:
a shoulder disposed about the first portion; and
an annular ring disposed about the second portion, wherein the shoulder is configured to abut the annular ring.

15. The patch pump system of claim 1, wherein the filling adapter comprises at least one locking tab comprising a cantilevered section in a circumferential wall of the second portion, wherein the at least one locking tab comprises a keyed end.

16. The patch pump system of claim 15, wherein the at least one locking tab is formed between axially-oriented slits in the circumferential wall of the second portion.

17. A method of filling a patch pump device, the method including the steps of:
coupling a first end of a first portion of a filling adapter to a medicament container;
locking a second end of a second portion of the filling adapter to a filling port on a patch pump device to rotate a shutter proximate the filling port about a pin from a closed position preventing access to the filing port to an open position allowing access to the filling port, wherein the shutter comprises:
a central portion and at least one wing portion extending therefrom, wherein the at least one wing portion is configured to prevent access to the filling port in the closed position, and
an opening disposed in the central portion, wherein the opening is configured to receive the pin therein;
engaging a protrusion disposed on a rim of the second portion with the opening of the central portion of the shutter to rotate the shutter from the closed position to the open position upon rotation of the filling adapter; and
filling a reservoir of the patch pump device with medicament from the medicament container via the filling port.

18. The method of claim 17, wherein coupling the first end of the filling adapter to the medicament container comprises receiving at least a portion of the medicament container in a recess of the filling adapter.

19. The method of claim 17, wherein coupling the first end of the filling adapter to the medicament container comprises piercing the medicament container with a needle.

20. The method of claim 17, wherein coupling the second end of the filling adapter to the filling port on the patch pump device comprises inserting a mating surface of the second end into the patch pump device.

21. The method of claim 17, wherein the medicament container comprises at least one of a syringe, a pen, a cartridge, and a vial.

22. The method of claim 17, wherein filling the reservoir comprises transferring medicament from the medicament container under pressure.

23. The method of claim 17 further comprising, after coupling the first end of the filling adapter to the medicament container, drawing medicament into the medicament container.

* * * * *